United States Patent
Touge et al.

(10) Patent No.: US 8,969,609 B1
(45) Date of Patent: Mar. 3, 2015

(54) RUTHENIUM-DIAMINE COMPLEX AND METHOD FOR PRODUCING OPTICALLY ACTIVE COMPOUND

(71) Applicant: Takasago International Corporation, Tokyo (JP)

(72) Inventors: Taichiro Touge, Hiratsuka (JP); Tomohiko Hakamata, Hamamatsu (JP); Hideki Nara, Fujisawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 14/528,093

(22) Filed: Oct. 30, 2014

Related U.S. Application Data

(62) Division of application No. 14/114,268, filed as application No. PCT/JP2012/061582 on May 2, 2012, now Pat. No. 8,901,323.

(30) Foreign Application Priority Data

May 6, 2011 (JP) ................................ 2011-103621

(51) Int. Cl.
C07F 15/00 (2006.01)
(52) U.S. Cl.
CPC .................................. C07F 15/0046 (2013.01)
USPC ...................................................... 556/136
(58) Field of Classification Search
USPC ....................................................... 556/136
See application file for complete search history.

(56) References Cited

U.S. PATENT DOCUMENTS

| | | | |
|---|---|---|---|
| 2011/0105693 A1 | 5/2011 | Abdur-Rashid et al. | |
| 2012/0123142 A1 | 5/2012 | Dyke et al. | |
| 2013/0123490 A1 | 5/2013 | Wisdom et al. | |
| 2013/0158276 A1 | 6/2013 | Touge et al. | |

FOREIGN PATENT DOCUMENTS

| | | |
|---|---|---|
| WO | 2009/132443 A1 | 11/2009 |
| WO | 2010/106364 A2 | 9/2010 |
| WO | 2011/131315 A1 | 10/2011 |
| WO | 2012/026201 A1 | 3/2012 |

OTHER PUBLICATIONS

Grazia Zassinovich et al., "Asymmetric Hydrogen Transfer Reactions Promoted by Homogeneous Transition Metal Catalysts," Chem. Rev. 1992, pp. 1051-1069, vol. 92, No. 5.
Shohei Hashiguchi et al., "Asymmetric Transfer Hydrogenation of Aromatic Ketones Catalyzed by Chiral Ruthenium(II) Complexes," J. Am. Chem. Soc., 1995, pp. 7562-7563, vol. 117, No. 28.
Akio Fujii et al., "Ruthenium(II)-Catalyzed Asymmetric Transfer Hydrogenation of Ketones Using a Formic Acid-Triethylamine Mixture," J. Am. Chem. Soc., 1996, pp. 2521-2522, vol. 118, No. 10.
Nobuyuki Uematsu et al., "Asymmetric Transfer Hydrogenation of Imines," J. Am. Chem. Soc., 1996, pp. 4916-4917, vol. 118, No. 20.
Aidan M. Hayes et al., "A Class of Ruthenium(II) Catalyst for Asymmetric Transfer Hydrogenations of Ketones," J. Am. Chem. Soc., 2005, pp. 7318-7319, vol. 127, No. 20.
David J. Morris et al., "The 'Reverse-Tethered' Ruthenium (II) Catalyst for Asymmetric Transfer Hydrogenation: Further Applications," J. Org. Chem., 2006, pp. 7035-7044, vol. 71, No. 18.
Fung Kei Cheung et al., "The use of a [4 + 2] cycloaddition reaction for the preparation of a series of 'tethered' Ru(II)-diamine and aminoalcohol complexes," Org. Biomol. Chem., 2007, pp. 1093-1103, vol. 5.
Fung K. Cheung et al., "An Investigation into the Tether Length and Substitution Pattern of Arene-Substituted Complexes for Asymmetric Transfer Hydrogenation of Ketones," Org. Lett., 2007, pp. 4659-4662, vol. 9., No. 22.
Jose E.D. Martins et al., "Further 'tethered' Ru(II) catalysts for asymmetric transfer hydrogenation (ATH) of ketones; the use of a benzylic linker and a cyclohexyldiamine ligand," Journal of Organomettalic Chemistry, 2008, pp. 3527-3532, vol. 693.
Fung Kei Cheung et al., "Kinetic and structural studies on 'tethered' Ru(II) arene ketone reduction catalysts," Dalton Trans., 2010, pp. 1395-1402, vol. 39.
International Searching Authority, International Search Report issued in PCT/JP2012/061582 dated Jul. 24, 2012.

(Continued)

*Primary Examiner* — Kristin Vajda
(74) *Attorney, Agent, or Firm* — Sughrue Mion, PLLC

(57) ABSTRACT

Provided is a ruthenium complex that is represented by general formula (1*) and is useful as an asymmetric reduction catalyst. (In the formula, * is an asymmetric carbon atom; $R^1$ is an arenesulfonyl group, and the like; $R^2$ and $R^3$ are a phenyl group, and the like; $R^{10}$ through $R^{14}$ are selected from a hydrogen atom, $C_{1-10}$ alkyl group, and the like, but $R^{10}$ through $R^{14}$ are not simultaneously hydrogen atoms; X is a halogen atom and the like; j and k are each either 0 or 1; and j+k is 0 or 2.)

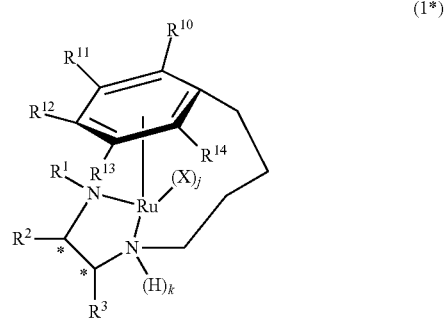

2 Claims, No Drawings

(56) References Cited

OTHER PUBLICATIONS

Taichiro Touge et al., "Oxo-Tethered Ruthenium(II) Complex as a Bifunctional Catalyst for Asymmetric Transfer Hydrogenation and H2 Hydrogenation," J. Am. Chem. Soc., 2011, pp. 14960-14963, vol. 133, No. 38.

Vimal Parekh et al., "Asymmetric transfer hydrogenation of quinolines using tethered Ru(II) catalysts," Tetrahedron: Asymmetry, 2010, pp. 1549-1556, vol. 21.

RUTHENIUM-DIAMINE COMPLEX AND METHOD FOR PRODUCING OPTICALLY ACTIVE COMPOUND

CROSS REFERENCE TO RELATED APPLICATIONS

The present application is a divisional of U.S. application Ser. No. 14/114,268 filed Oct. 28, 2013, which is a National Stage of International Application No. PCT/JP2012/061582, filed on May 2, 2012, which claims the benefit of priority from Japanese Patent Application No. JP 2011-103621, filed on May 6, 2011, the contents of which are herein incorporated by reference in their entirety.

TECHNICAL FIELD

The present invention relates to a novel ruthenium-diamine complex, and a method for selectively producing optically active alcohols and optically active amines, which are important as precursors for synthesizing pharmaceuticals and functional materials, the method using the ruthenium-diamine complex as a catalyst.

BACKGROUND ART

Many asymmetric reactions including asymmetric reduction have been developed, and many asymmetric reactions have been reported in which asymmetric metal complexes having optically active phosphine ligands are used. On the other hand, many reports have shown that complexes in which optically active nitrogen compounds are coordinated to transition metals, such as ruthenium, rhodium, and iridium, for example, have excellent performances as catalysts for asymmetric synthesis reactions. Moreover, to enhance the performances of these catalysts, various optically active nitrogen compounds have been developed (Non Patent Literatures 1, 2, 3, 4, etc.). In particular, M. Wills et al. have reported that complexes in which a diamine moiety and an aromatic ring (arene) moiety coordinated to the ruthenium complex are linked by a carbon chain exhibit higher activities than conventional catalysts (Non Patent Literatures 5, 6, 7, 8, 9, 10, etc.).

CITATION LIST

Non Patent Literatures

Non Patent Literature 1: Chem. Rev. (1992), p. 1051
Non Patent Literature 2: J. Am. Chem. Soc. 117 (1995), p. 7562
Non Patent Literature 3: J. Am. Chem. Soc. 118 (1996), p. 2521
Non Patent Literature 4: J. Am. Chem. Soc. 118 (1996), p. 4916
Non Patent Literature 5: J. Am. Chem. Soc. 127 (2005), p. 7318
Non Patent Literature 6: J. Org. Chem. 71 (2006), p. 7035
Non Patent Literature 7: Org. Biomol. Chem. 5 (2007), p. 1093
Non Patent Literature 8: Org. Lett. 9 (2007), p. 4659
Non Patent Literature 9: J. Organometallic. Chem. 693 (2008), p. 3527
Non Patent Literature 10: Dalton. Trans. 39 (2010), p. 1395

SUMMARY OF INVENTION

However, conventional asymmetric synthesis methods using any of these complexes result in insufficient catalytic activity or insufficient enantiomeric excess in some cases depending on the target reaction or the reaction substrate of the reaction. Hence, further development of a complex has been desired.

The present inventors have focused on the chain moiety which links the arene moiety coordinated to ruthenium and the diamine moiety, and have found that a complex in which (i) at least one substituent is present on the aromatic ring in the arene moiety, and (ii) the length of the carbon chain of the linking chain moiety is 4 has a high catalytic activity and achieves an excellent enantiomeric excess.

Specifically, the present invention includes the following contents.

[1] A ruthenium complex represented by the following general formula (1):

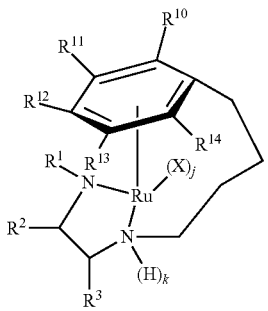

(1)

wherein $R^1$ represents an alkyl group having 1 to 10 carbon atoms; an alkanesulfonyl group having 1 to 10 carbon atoms and optionally substituted with a halogen atom; an arenesulfonyl group optionally substituted with an alkyl group having 1 to 10 carbon atoms, a halogenated alkyl group having 1 to 10 carbon atoms, or a halogen atom; an alkoxycarbonyl group having 2 to 11 carbon atoms in total; or a benzoyl group optionally substituted with an alkyl group having 1 to 10 carbon atoms, $R^2$ and $R^3$ each independently represent an alkyl group having 1 to 10 carbon atoms; a phenyl group optionally substituted with an alkyl group having 1 to 10 carbon atoms, an alkoxy group having 1 to 10 carbon atoms, or a halogen atom; or a cycloalkyl group having 3 to 8 carbon atoms, or $R^2$ and $R^3$ may together form a ring, $R^{10}$ to $R^{14}$ each independently represent a hydrogen atom, an alkyl group having 1 to 10 carbon atoms, an alkoxy group having 1 to 10 carbon atoms, or a trialkylsilyl group, provided that the case where all of $R^{10}$ to $R^{14}$ simultaneously represent hydrogen atoms is excluded, X represents a trifluoromethanesulfonyloxy group, a p-toluenesulfonyloxy group, a methanesulfonyloxy group, a benzenesulfonyloxy group, a hydrogen atom, or a halogen atom, j and k each represent 0 or 1, and j+k is 0 or 2.

[2] A ruthenium complex represented by the following general formula (1*):

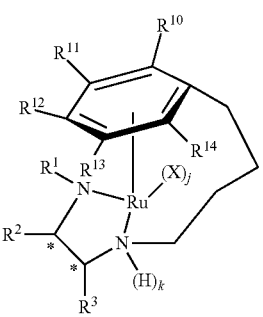

(1*)

wherein each * represents an asymmetric carbon atom, $R^1$ represents an alkyl group having 1 to 10 carbon atoms; an alkanesulfonyl group having 1 to 10 carbon atoms and optionally substituted with a halogen atom; an arenesulfonyl group optionally substituted with an alkyl group having 1 to 10 carbon atoms, a halogenated alkyl group having 1 to 10 carbon atoms, or a halogen atom; an alkoxycarbonyl group having 2 to 11 carbon atoms in total; or a benzoyl group optionally substituted with an alkyl group having 1 to 10 carbon atoms, $R^2$ and $R^3$ each independently represent an alkyl group having 1 to 10 carbon atoms; a phenyl group optionally substituted with an alkyl group having 1 to 10 carbon atoms, an alkoxy group having 1 to 10 carbon atoms, or a halogen atom; or a cycloalkyl group having 3 to 8 carbon atoms, or $R^2$ and $R^3$ may together form a ring, $R^{10}$ to $R^{14}$ each independently represent a hydrogen atom, an alkyl group having 1 to 10 carbon atoms, an alkoxy group having 1 to 10 carbon atoms, or a trialkylsilyl group, provided that the case where all of $R^{10}$ to $R^{14}$ simultaneously represent hydrogen atoms is excluded, X represents a trifluoromethanesulfonyloxy group, a p-toluenesulfonyloxy group, a methanesulfonyloxy group, a benzenesulfonyloxy group, a hydrogen atom, or a halogen atom, j and k each represent 0 or 1, and j+k is 0 or 2.

ally substituted with a halogen atom; an arenesulfonyl group optionally substituted with an alkyl group having 1 to 10 carbon atoms, a halogenated alkyl group having 1 to 10 carbon atoms, or a halogen atom; an alkoxycarbonyl group having 2 to 11 carbon atoms in total; or a benzoyl group optionally substituted with an alkyl group having 1 to 10 carbon atoms, $R^2$ and $R^3$ each independently represent an alkyl group having 1 to 10 carbon atoms; a phenyl group optionally substituted with an alkyl group having 1 to 10 carbon atoms, an alkoxy group having 1 to 10 carbon atoms, or a halogen atom; or a cycloalkyl group having 3 to 8 carbon atoms, or $R^2$ and $R^3$ may together form a ring, $R^{10}$ to $R^{14}$ each independently represent a hydrogen atom, an alkyl group having 1 to 10 carbon atoms, an alkoxy group having 1 to 10 carbon atoms, or a trialkylsilyl group, provided that the case where all of $R^{10}$ to $R^{14}$ simultaneously represent hydrogen atoms is excluded, and $Q^-$ represents a counter anion.

[4] A ruthenium complex represented by the following general formula (2), or a salt thereof:

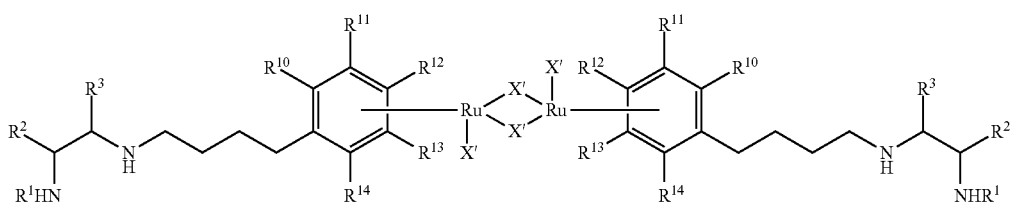

(2)

[3] A ruthenium complex represented by the following general formula (1'):

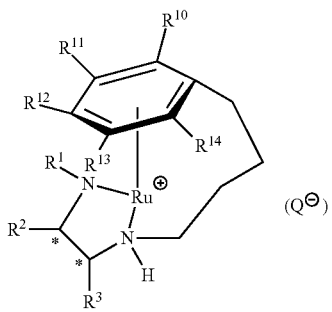

(1')

wherein $R^1$ represents an alkyl group having 1 to 10 carbon atoms; an alkanesulfonyl group having 1 to 10 carbon atoms and optionally substituted with a halogen atom; an arenesulfonyl group optionally substituted with an alkyl group having 1 to 10 carbon atoms, a halogenated alkyl group having 1 to 10 carbon atoms, or a halogen atom; an alkoxycarbonyl group having 2 to 11 carbon atoms in total; or a benzoyl group optionally substituted with an alkyl group having 1 to 10 carbon atoms, $R^2$ and $R^3$ each independently represent an alkyl group having 1 to 10 carbon atoms; a phenyl group optionally substituted with an alkyl group having 1 to 10 carbon atoms, an alkoxy group having 1 to 10 carbon atoms, or a halogen atom; or a cycloalkyl group having 3 to 8 carbon atoms, or $R^2$ and $R^3$ may together form a ring, $R^{10}$ to $R^{14}$ each independently represent a hydrogen atom, an alkyl group having 1 to 10 carbon atoms, an alkoxy group having 1 to 10 carbon atoms, or a trialkylsilyl group, provided that the case where all of $R^{10}$ to $R^{14}$ simultaneously represent hydrogen atoms is excluded, and X' represents a halogen atom.

wherein each * represents an asymmetric carbon atom, $R^1$ represents an alkyl group having 1 to 10 carbon atoms; an alkanesulfonyl group having 1 to 10 carbon atoms and option-

[5] A ruthenium complex represented by the following general formula (2*), or a salt thereof:

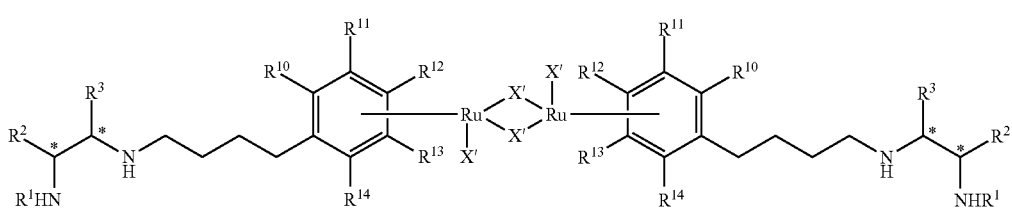

(2*)

wherein each * represents an asymmetric carbon atom, $R^1$ represents an alkyl group having 1 to 10 carbon atoms; an alkanesulfonyl group having 1 to 10 carbon atoms and optionally substituted with a halogen atom; an arenesulfonyl group optionally substituted with an alkyl group having 1 to 10 carbon atoms, a halogenated alkyl group having 1 to 10 carbon atoms, or a halogen atom; an alkoxycarbonyl group having 2 to 11 carbon atoms in total; or a benzoyl group optionally substituted with an alkyl group having 1 to 10 carbon atoms, $R^2$ and $R^3$ each independently represent an alkyl group having 1 to 10 carbon atoms; a phenyl group optionally substituted with an alkyl group having 1 to 10 carbon atoms, an alkoxy group having 1 to 10 carbon atoms, or a halogen atom; or a cycloalkyl group having 3 to 8 carbon atoms, or $R^2$ and $R^3$ may together form a ring, $R^{10}$ to $R^{14}$ each independently represent a hydrogen atom, an alkyl group having 1 to 10 carbon atoms, an alkoxy group having 1 to 10 carbon atoms, or a trialkylsilyl group, provided that the case where all of $R^{10}$ to $R^{14}$ simultaneously represent hydrogen atoms is excluded, and X' represents a halogen atom.

[6] A catalyst for asymmetric reduction, comprising the ruthenium complex according to [2], [3], or [5].

[7] A method for producing an optically active alcohol, comprising reducing a carbonyl group of a carbonyl compound in the presence of the ruthenium complex according to [2], [3], or [5] and a hydrogen donor.

[8] A method for producing an optically active amine, comprising reducing an imino group of an imine compound in the presence of the ruthenium complex according to [2], [3], or [5] and a hydrogen donor.

[9] The production method according to [7] or [8], wherein the hydrogen donor is selected from formic acid, alkali metal formates, and alcohols having a hydrogen atom on a carbon atom at an α-position of a carbon atom substituted with a hydroxyl group.

[10] The production method according to [7] or [8], wherein the hydrogen donor is hydrogen gas.

The present invention provides a novel ruthenium-diamine complex in which a diamine moiety and an arene moiety coordinated to the ruthenium complex is linked by a carbon chain. The ruthenium-diamine complex of the present invention has an extremely higher catalytic activity than conventional hydrogen transfer-type complexes, and hence is useful as various hydrogenation catalysts. Moreover, the ruthenium complex of the present invention in which a substituent such as an alkyl group is present on the aromatic ring and the length of the carbon chain of the linking chain moiety is 4 is excellent in stereoselectivity and achieves a high enantiomeric excess, and hence makes it possible to obtain a target substance with a high optical purity and a high yield in a hydrogen transfer reaction or a hydrogenation reaction.

The use of the ruthenium-diamine complex of the present invention makes it possible to selectively produce optically active alcohols and optically active amine, which are useful as a raw material for producing pharmaceuticals and functional materials and the like.

DESCRIPTION OF EMBODIMENTS

Hereinafter, the present invention will be described in further detail.

In the ruthenium complex represented by each of the general formulae (1), (1*), (1'), (2), and (2*), the alkyl group having 1 to 10 carbon atoms represented by $R^1$ is a linear or branched alkyl group having 1 to 10 carbon atoms, and preferably 1 to 5 carbon atoms. Specific examples of the alkyl group include a methyl group, an ethyl group, a n-propyl group, an isopropyl group, a n-butyl group, an isobutyl group, a s-butyl group, a t-butyl group, a n-pentyl group, a n-hexyl group, a n-heptyl group, a n-octyl group, a n-nonyl group, a n-decyl group, and the like.

Examples of the alkanesulfonyl group having 1 to 10 carbon atoms represented by $R^1$ include a methanesulfonyl group, an ethanesulfonyl group, a propanesulfonyl group, and the like. The alkanesulfonyl group is optionally substituted with one or multiple halogen atoms. Examples of the halogen atoms include chlorine atoms, bromine atoms, fluorine atoms, and the like. Examples of the alkanesulfonyl group having 1 to 10 carbon atoms and substituted with a halogen atom include a trifluoromethanesulfonyl group, and the like.

Examples of the arenesulfonyl group represented by $R^1$ include a benzenesulfonyl group, and the like. The arenesulfonyl group is optionally substituted with one or multiple alkyl groups having 1 to 10 carbon atoms, halogenated alkyl groups having 1 to 10 carbon atoms, or halogen atoms. The alkyl groups having 1 to 10 carbon atoms include those listed as the alkyl group having 1 to 10 carbon atoms represented by $R^1$, and the like. The halogenated alkyl groups having 1 to 10 carbon atoms include halides of those listed as the alkyl group having 1 to 10 carbon atoms represented by $R^1$ (examples of the halogen atoms include chlorine atoms, bromine atoms, fluorine atoms, and the like), and the like.

Examples of the halogen atoms include chlorine atoms, bromine atoms, fluorine atoms, and the like. Examples of the arenesulfonyl group substituted with an alkyl group having 1 to 10 carbon atoms, a halogenated alkyl group having 1 to 10 carbon atoms, or a halogen atom include a p-toluenesulfonyl group, a 2,4,6-trimethylbenzenesulfonyl group, a 4-trifluoromethylbenzenesulfonyl group, a pentafluorobenzenesulfonyl group, and the like.

The alkoxycarbonyl group having 2 to 11 carbon atoms in total represented by $R^1$ may be a linear or branched alkoxycarbonyl group preferably having 2 to 5 carbon atoms in total, and specifically is a methoxycarbonyl group, an ethoxycarbonyl group, a t-butoxycarbonyl group, or the like.

The benzoyl group represented by $R^1$ is optionally substituted with one or multiple alkyl groups having 1 to 10 carbon atoms. The alkyl groups having 1 to 10 carbon atoms include those listed as the alkyl group having 1 to 10 carbon atoms represented by $R^1$, and the like. The benzoyl group optionally substituted with an alkyl group having 1 to 10 carbon atoms is a benzoyl group, a p-toluoyl group, an o-toluoyl group, or the like.

The alkyl group having 1 to 10 carbon atoms represented by each of $R^2$ and $R^3$ includes those listed as the alkyl group having 1 to 10 carbon atoms represented by $R^1$, and the like.

The phenyl group represented by each of $R^2$ and $R^3$ is optionally substituted with one or multiple alkyl groups having 1 to 10 carbon atoms, alkoxy groups having 1 to 10 carbon atoms, or halogen atoms. The alkyl groups having 1 to 10 carbon atoms include those listed as the alkyl group having 1 to 10 carbon atoms represented by $R^1$, and the like. The alkoxy groups having 1 to 10 carbon atoms are linear or branched alkoxy groups having 1 to 10 carbon atoms, and preferably 1 to 5 carbon atoms. Specific examples of the alkoxy groups include methoxy groups, ethoxy groups, n-propoxy groups, isopropoxy groups, n-butoxy groups, isobutoxy groups, s-butoxy groups, t-butoxy groups, n-pentyloxy groups, n-hexyloxy groups, n-heptyloxy groups, n-octyloxy groups, n-nonyloxy groups, n-decyloxy groups, and the like. Examples of the halogen atoms include chlorine atoms, bromine atoms, fluorine atoms, and the like. Examples of the phenyl group substituted with an alkyl group having 1 to 10 carbon atoms, an alkoxy group having 1 to 10 carbon atoms, or a halogen atom include a 2,4,6-trimethylphenyl group, a 4-methoxyphenyl group, a 2,4,6-trimethoxyphenyl group, a 4-fluorophenyl group, a 2-chlorophenyl group, a 4-chlorophenyl group, a 2,4-dichlorophenyl group, and the like.

The cycloalkyl group having 3 to 8 carbon atoms represented by each of $R^2$ and $R^3$ is a monocyclic, polycyclic, or bridged cycloalkyl group having 3 to 8 carbon atoms, and preferably 5 to 8 carbon atoms. Specific examples of the cycloalkyl group having 3 to 8 carbon atoms include a cyclopropyl group, a cyclobutyl group, a cyclopentyl group, a cyclohexyl group, a cycloheptyl group, a cyclooctyl group, and the like. These cycloalkyl groups are optionally substituted with alkyl groups such as methyl groups, isopropyl groups, and t-butyl groups, or the like.

Regarding the ring formed by $R^2$ and $R^3$ together, $R^2$ and $R^3$ together form a linear or branched alkylene group having 2 to 10 carbon atoms, and preferably 3 to 10 carbon atoms, and thus form a preferably 4- to 8-membered, more preferably 5- to 8-membered cycloalkane ring together with the adjacent carbon atoms. Preferred examples of the cycloalkane ring include a cyclopentane ring, a cyclohexane ring, and a cycloheptane ring. These rings may have, as substituents, alkyl groups such as methyl groups, isopropyl groups, and t-butyl group, or the like.

The alkyl group having 1 to 10 carbon atoms represented by each of $R^{10}$ to $R^{14}$ is a linear or branched alkyl group having 1 to 10 carbon atoms, and preferably 1 to 5 carbon atoms. Specific examples of the alkyl group include a methyl group, an ethyl group, a n-propyl group, an isopropyl group, a n-butyl group, an isobutyl group, a s-butyl group, a t-butyl group, a n-pentyl group, a n-hexyl group, a n-heptyl group, a n-octyl group, a n-nonyl group, a n-decyl group, and the like.

The alkoxy group having 1 to 10 carbon atoms represented by each of $R^{10}$ to $R^{14}$ is a linear or branched alkoxy group having 1 to 10 carbon atoms, and preferably 1 to 5 carbon atoms. Specific examples of the alkoxy group include a methoxy group, an ethoxy group, a n-propoxy group, an isopropoxy group, a n-butoxy group, an isobutoxy group, a s-butoxy group, a t-butoxy group, a n-pentyloxy group, a n-hexyloxy group, a n-heptyloxy group, a n-octyloxy group, a n-nonyloxy group, a n-decyloxy group, and the like.

The alkyl groups of the trialkylsilyl group represented by each of $R^{10}$ to $R^{14}$ are alkyl groups having 1 to 10 carbon atoms, and are specifically methyl groups, ethyl groups, n-propyl groups, isopropyl groups, n-butyl groups, isobutyl groups, s-butyl groups, t-butyl groups, n-pentyl groups, n-hexyl groups, n-heptyl groups, n-octyl groups, n-nonyl groups, n-decyl groups, or the like. Specific examples of the trialkylsilyl group include a trimethylsilyl group, a triethylsilyl group, a t-butyldimethylsilyl group, a triisopropylsilyl group, and the like.

Note that the case where all of $R^{10}$ to $R^{14}$ simultaneously represent hydrogen atoms is excluded.

In the ruthenium complex represented by the general formula (1) or (1*), j and k are each an integer of 0 or 1, provided that the case where j+k is 1 is excluded. In other words, when k is 1, j is also 1, whereas when k is 0, j is also 0.

When j is 1 in the ruthenium complex represented by the general formula (1) or (1*), X represents a trifluoromethanesulfonyloxy group, a p-toluenesulfonyloxy group, a methanesulfonyloxy group, a benzenesulfonyloxy group, a hydrogen atom, or a halogen atom, and preferably is a halogen atom. The halogen atom is preferably a chlorine atom.

In the ruthenium complex represented by the general formula (2) or (2*), the halogen atom represented by X' is preferably a chlorine atom.

$Q^-$ in the general formula (1') represents a counter anion. The counter anion is specifically an ion such as $BF_4^-$, $SbF_6^-$, $CF_3COO^-$, $CH_3COO^-$, $PF_6^-$, $NO_3^-$, $ClO_4^-$, $SCN^-$, $OCN^-$, $ReO_4^-$, $MoO_4^-$, $BPh_4^-$, $B(C_6F_5)_4^-$, or $B(3,5-(CF_3)_2C_6F_3)_4^-$.

The ruthenium complex represented by each of the general formulae (1), (1*), (2), and (2*) of the present invention can be produced, for example, by a method according to Scheme 1 below. Note that although a case of the general formula (1*) or (2*) which represents an optically active substance is described in Scheme 1, a non-optically active substance of the general formula (1) or (2) can also be produced by the same method.

Scheme 1

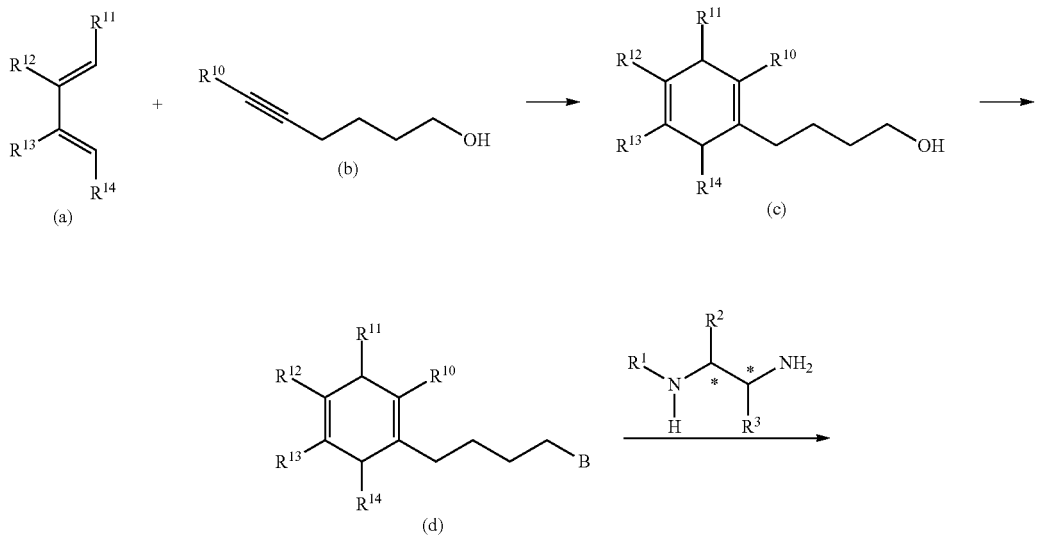

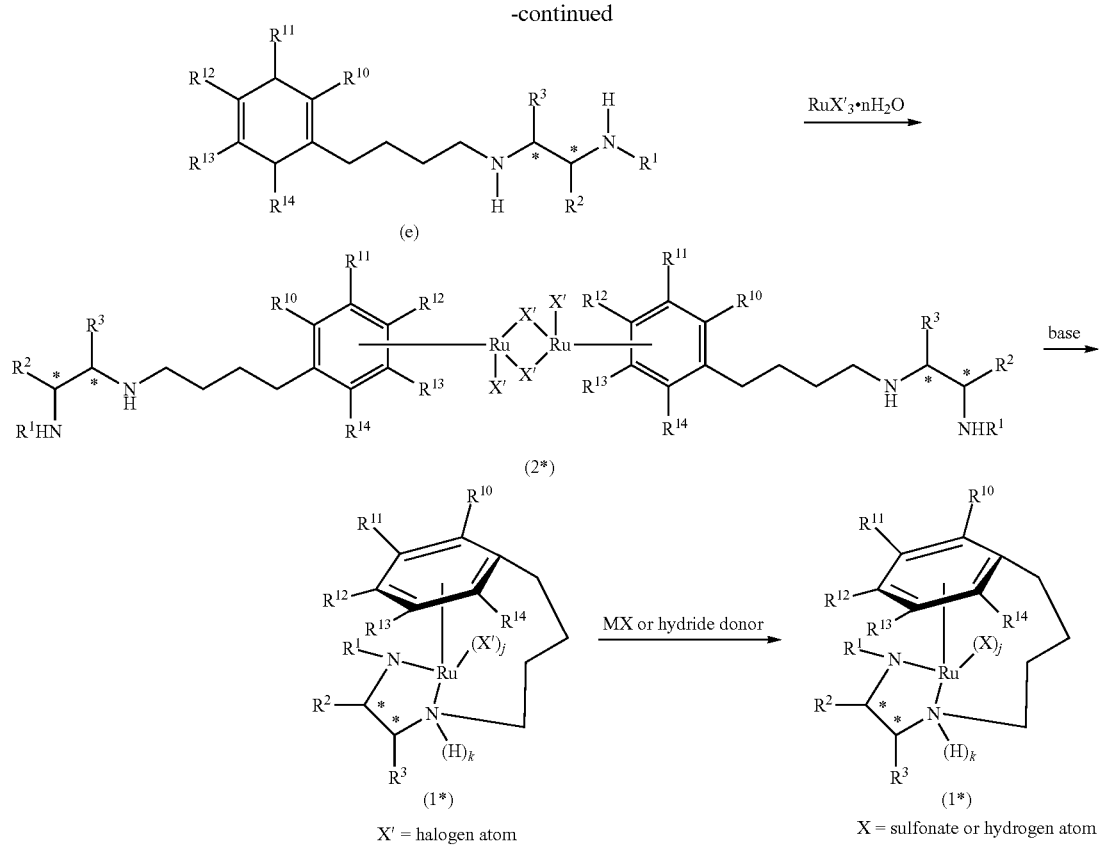

wherein $R^1$ to $R^3$, $R^{10}$ to $R^{14}$, X, X', j, and k are the same as those described above, B is a leaving group, and M represents an alkali metal or a hydrogen atom.

The alcohol (c) can be synthesized by a Diels-Alder reaction of the diene (a) having substituents and the alkyne (b) having a substituent. The reagent used is a metal complex such as [1,2-bis(diphenylphosphino)ethane]cobalt(II) dibromide, 1,5-cyclooctadiene(naphthalene)rhodium(I) tetrafluoroborate, dichloro(1,4-diaza-1,3-diene)iron(II), or dichlorobis(tri-o-biphenylphosphite)nickel(II). A solvent used for the Diels-Alder reaction is not particularly limited, unless the reaction is adversely affected. Examples of the solvent include ethers such as diethyl ether, tetrahydrofuran, and dioxane; aromatic hydrocarbons such as toluene and xylene; halogen-containing hydrocarbon solvents such as dichloromethane and 1,2-dichloroethane; aprotic polar solvents such as acetonitrile, ethyl acetate, and acetone; and the like. Dichloromethane or tetrahydrofuran is particularly preferable. The reaction temperature of the Diels-Alder reaction is in a range of generally −20° C. to 100° C., and preferably 10° C. to 40° C., although it naturally varies depending on the substrate used. In addition, the reaction time of the Diels-Alder reaction is generally 30 minutes to 30 hours, and preferably 1 hour to 20 hours, although it naturally varies depending on the substrate used. Note that the Diels-Alder reaction is preferably performed in an inert gas such as nitrogen or argon.

Next, the hydroxyl group moiety of the alcohol (c) is converted to a leaving group such as a halogen atom, an alkanesulfonyloxy group, or an arenesulfonyloxy group, and thus the compound represented by the general formula (d) is synthesized. The reagent used here is hydrogen chloride, thionyl chloride, sulfuryl chloride, oxalyl chloride, phosphorus trichloride, phosphorus pentachloride, hydrogen bromide, phosphorus tribromide, phosphorus pentabromide, carbon tetrabromide, dimethylbromosulfonium bromide, thionyl bromide, hydrogen iodide, phosphorus triiodide, triphenyl phosphite methiodide, p-toluenesulfonyl chloride, methanesulfonyl chloride, trifluoromethanesulfonyl chloride, trifluoromethanesulfonic anhydride, or the like. The reaction solvent is not particularly limited, and examples thereof include ethers such as diethyl ether, tetrahydrofuran, and dioxane; aromatic hydrocarbons such as benzene, toluene, and xylene; halogen-containing hydrocarbon solvents such as dichloromethane and 1,2-dichloroethane; aprotic polar solvents such as N,N-dimethylformamide, acetonitrile, and dimethyl sulfoxide; alcohols such as methanol, ethanol, and 2-propanol; and the like. Dichloromethane, tetrahydrofuran, or toluene is particularly preferable. Note that, for some reaction systems, it is preferable to perform this reaction in the presence of a base in an amount of 1 to 2 equivalents to the reaction substrate. The reaction temperature is in a range of generally −30° C. to 200° C., and preferably 10° C. to 100° C., although it naturally varies depending on the substrate used. In addition, the reaction time is generally 30 minutes to 30 hours, and preferably 1 hour to 20 hours, although it naturally varies depending on the substrate used. Note that the reaction is preferably performed in an inert gas such as nitrogen or argon.

Next, a solvent used for synthesizing a compound represented by the general formula (e) from the compound represented by the general formula (d) and a diamine compound is preferably an ether such as 1,4-dioxane; an aromatic hydrocarbon such as toluene, xylene, or mesitylene; a halogen-containing aromatic hydrocarbon such as chlorobenzene; an aprotic polar solvent such as N,N-dimethylformamide or dimethyl sulfoxide; or the like, and is particularly preferably dimethyl sulfoxide, toluene, xylene, or mesitylene, although the solvent is not particularly limited. In addition, the reaction can also be performed in a mixture solvent of an organic solvent with water by using water as another solvent. Meanwhile, the base used for the reaction is preferably an inorganic base such as sodium hydroxide, sodium hydrogen carbonate, sodium carbonate, potassium hydroxide, potassium hydrogen carbonate, potassium carbonate, lithium hydroxide, lithium hydrogen carbonate, lithium carbonate, cesium carbonate, magnesium hydroxide, magnesium carbonate, calcium hydroxide, or calcium carbonate; or a tertiary organic amine such as trimethylamine, triethylamine, triisopropylamine, tributylamine, or diisopropylethylamine, and is particularly preferably triethylamine or diisopropylethylamine. The amount of the base used is 0.2 to 2 equivalents, and preferably 1 to 1.5 equivalents to the compound represented by the general formula (d). The reaction temperature is, for example, 100° C. to 200° C., and preferably 100° C. to 160° C. The reaction time is 30 minutes to 30 hours, and preferably 1 hour to 12 hours, although it varies depending on the reaction substrate used. The reaction is preferably performed in an inert gas such as nitrogen gas or argon gas. Moreover, an additive such as sodium iodide, potassium iodide, lithium iodide, sodium bromide, potassium bromide, lithium bromide, potassium chloride, or lithium chloride may be added. The additive is preferably potassium iodide or lithium iodide. The amount of the additive is 0 to 10 equivalents, and preferably 0.1 to 1 equivalents to the compound represented by the general formula (d).

From the compound of the general formula (e), the ruthenium-diamine complex (1) can be produced according to the description in Org. Lett. 9 (2007), p. 4659, for example.

A solvent used for synthesizing the ruthenium dimer complex of the general formula (2) from the compound of the general formula (e) and RuX'$_3$.nH$_2$O (for example, ruthenium (III) chloride or hydrate thereof) is not particularly limited, and is an aliphatic alcohol such as 2-propanol, n-butanol, 2-butanol, n-pentanol, 2-pentanol, 3-pentanol, 3-methyl-1-butanol, cyclopentanol, 3-methoxy-1-propanol, 2-methoxyethanol, 2-ethoxyethanol, 2-isopropoxyethanol, n-hexanol, 3-methoxy-1-butanol, 3-methoxy-3-methyl-1-butanol, 2-hexanol, 3-hexanol, cyclohexanol, n-heptanol, 2-heptanol, 3-heptanol, cycloheptanol, n-octanol, 2-octanol, 3-octanol, 4-octanol, or cyclooctanol; an aromatic alcohol such as phenol, benzyl alcohol, 1-phenylethanol, 2-phenylethanol, o-cresol, m-cresol, p-cresol, 2-methylbenzyl alcohol, 3-methylbenzyl alcohol, or 4-methylbenzyl alcohol; a diol such as ethylene glycol, 1,2-propanediol, 1,3-propanediol, 1,2-butanediol, 1,3-butanediol, 1,4-butanediol, ethylene glycol-n-butyl ether, ethylene glycol-iso-butyl ether, or ethylene glycol-n-hexyl ether; a derivative thereof; or the like. One of these solvents may be used alone, or two or more thereof may be used as a mixture. By using two or more solvents in combination, the boiling point of the solvent can be adjusted in a desired range, so that the reaction temperature can be controlled for the reaction under reflux. For example, an alcohol with which a small amount of water is mixed may be used. The amount of the compound of the general formula (e) used is 1 to 20 equivalents, preferably 1 to 10 equivalents, and more preferably 1 to 5 equivalents to ruthenium atoms. The amount of the solvent used is not particularly limited, as long as ruthenium chloride or hydrate thereof can be dissolved therein at the reaction temperature. For example, the amount of the solvent is 2 to 50 times volume (i.e., 2 to 50 mL of the solvent relative to 1 g of ruthenium chloride or hydrate thereof), preferably 2 to 30 times volume, and more preferably 5 to 20 times volume of ruthenium chloride or hydrate thereof. From the viewpoint of reaction efficiency, the reaction temperature is 60° C. or above, and preferably 100° C. or above, and also 200° C. or below, and preferably 160° C. or below, although it varies depending on the solvent used.

A solvent used for synthesizing the ruthenium complex of the general formula (1) from the ruthenium dimer complex of the general formula (2) is not particularly limited, and is a halogenated solvent such as methylene chloride, dichloroethane, chloroform, or trifluoroethanol; an aromatic hydrocarbon such as toluene or xylene; an ether such as diisopropyl ether or tetrahydrofuran; an alcohol such as methanol, ethanol, 2-propanol, n-butanol, 2-butanol, or n-pentanol; or the like. Dichloromethane or isopropanol is particularly preferable. One of these solvents may be used alone, or two or more thereof may be used as a mixture. By using two or more solvents in combination, the boiling point of the solvent can be adjusted in a desired range, so that the reaction temperature can be controlled for the reaction under reflux. For example, an alcohol with which a small amount of water is mixed may be used. The base used here is an inorganic base such as sodium hydroxide, sodium hydrogen carbonate, sodium carbonate, potassium hydroxide, potassium hydrogen carbonate, potassium carbonate, lithium hydroxide, lithium hydrogen carbonate, lithium carbonate, cesium carbonate, magnesium hydroxide, magnesium carbonate, calcium hydroxide, or calcium carbonate; an amine such as triethylamine, tripropylamine, tributylamine, pyridine, or triisopropylamine; or the like. Triethylamine is particularly preferable. The amount of the base used is 0.2 to 2 equivalents, and preferably 1 to 1.5 equivalents to the ruthenium atoms. The reaction time is 30 minutes to 20 hours, and preferably 1 hour to 12 hours, although it varies depending on the reaction substrate used. The reaction is preferably performed in an inert gas such as nitrogen gas or argon gas.

By bringing the ruthenium complex of the general formula (1) in which X is a halogen atom, a trifluoromethanesulfonyloxy group, a p-toluenesulfonyloxy group, a methanesulfonyloxy group, or a benzenesulfonyloxy group into contact with a hydrogen donor, this ruthenium complex can be easily converted to a ruthenium complex of the general formula (1) in which X is a hydrogen atom. Here, as the hydrogen donor, those generally used as a hydrogen donor in a hydrogen transfer reduction reaction, such as formic acid, salts thereof, isopropanol, and metal hydrides including borohydride compounds, can be used. The amount of the hydrogen donor used only needs to be equimolar to the catalyst or more in terms of hydride. In addition, hydrogen gas can also be used as the hydrogen donor. In addition, a base used to achieve a basic condition in this reaction is a tertiary organic amine such as trimethylamine, triethylamine, or triisopropylamine; an inorganic base such as LiOH, NaOH, KOH, or K$_2$CO$_3$; or a metal alkoxide such as sodium methoxide or potassium methoxide.

In addition, the cationic ruthenium complex represented by the general formula (1') of the present invention can be obtained by, for example, by a method according to Scheme 2 below, i.e., by reacting the complex (1*) in which X is a halogen atom with a metal salt represented by M-Q.

Scheme 2

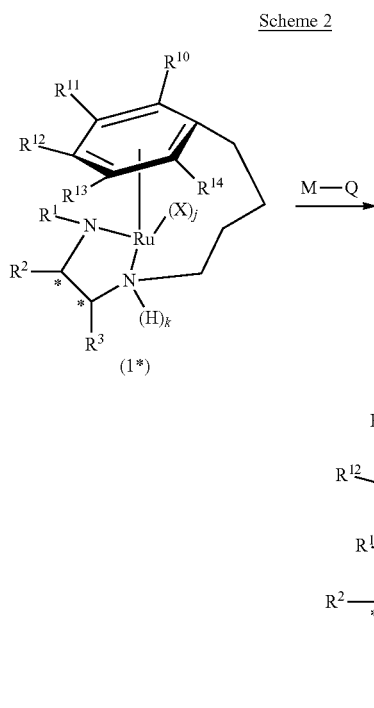

Examples of the metal M in M-Q include silver (Ag), sodium (Na), potassium (K), lithium (Li), and the like. Q is alkanesulfonyloxy or arene sulfonyloxy such as trifluoromethanesulfonyloxy (TfO), p-toluenesulfonyloxy (TsO), methanesulfonyloxy (MsO), or benzenesulfonyloxy (BsO), or the like. Alternatively, Q may be $BF_4$, $SbF_6$, $CF_3COO$, $CH_3COO$, $PF_6$, $NO_3$, $ClO_4$, $SCN$, $OCN$, $ReO_4$, $MoO_4$, $BPh_4$, $B(C_6F_5)_4$, $B(3,5-(CF_3)_2C_6F_3)_4$, or the like.

Examples of the metal salt represented by M-Q include AgOTf, AgOTs, AgOMs, AgOBs, $AgBE_4$, $AgSbF_6$, $CF_3COOAg$, $CH_3COOAg$, $AgPF_6$, $AgNO_3$, $AgClO_4$, AgSCN, AgOCN, $AgReO_4$, $AgMoO_4$, NaOTf, $NaBF_4$, $NaSbF_6$, $CF_3COONa$, $CH_3COONa$, $NaPF_6$, $NaNO_3$, $NaClO_4$, NaSCN, KOTf, $KBF_4$, $KSbF_6$, $CF_3COOK$, $CH_3COOK$, $KPF_6$, $KNO_3$, $KClO_4$, KSCN, $KBPh_4$, $KB(C_6F_5)_4$, $KB(3,5-(CF_3)_2C_6F_3)_4$, LiOTf, $LiBF_4$, $LiSbF_6$, $CF_3COOLi$, $CH_3COOLi$, $LiPF_6$, $LiNO_3$, $LiClO_4$, LiSCN, $LiBPh_4$, $LiB(C_6F_5)_4$, $LiB(3,5-(CF_3)_2C_6F_3)_4$, and the like.

The metal salt M-Q in Scheme 2 is used in an equimolar amount to the ruthenium atoms or more. A solvent used in this case is not particularly limited, and is an alcohol such as methanol, ethanol, or isopropanol; an aromatic hydrocarbon such as toluene or xylene; a halogenated hydrocarbon such as dichloromethane or 1,2-dichloroethane; an aprotic polar solvent such as acetonitrile or N,N-dimethylformamide; an ether such as diethyl ether or tetrahydrofuran; or the like. Of these solvents, methanol is preferable.

The ruthenium complex of each of the general formulae (1*), (1'), and (2*) can be used as a catalyst for asymmetric reduction. The asymmetric reduction reaction may be performed by using the prepared ruthenium complex of the general formula (1*) or (1') or the general formula (2*) as a catalyst for asymmetric reduction after isolation, or by directly using the reaction liquid in which the ruthenium complex is prepared without isolating the ruthenium complex (in situ method). Note that the ruthenium dimer complex of the general formula (2*) is preferably used after isolation. The ruthenium complex of the general formula (1*), (1'), or (2*) can be isolated by a common crystallization approach such as concentration of the reaction liquid or addition of a poor solvent after completion of the preparation reaction of the complex. In addition, when a hydrogen halide is by-produced in the preparation of the complex, a washing operation with water may be performed, if necessary. In addition, the conversion of the ruthenium complex of the general formula (1) in which X is a halogen atom or the like to the ruthenium complex of the general formula (1*) in which X is a hydrogen atom may be conducted in advance before the use for the asymmetric reduction reaction, or may be performed during the asymmetric reduction reaction.

The asymmetric reduction reactions include (i) reactions for preparing an optically active alcohol by reducing a carbonyl group of a carbonyl compound, and (ii) reactions for preparing an optically active amine by reducing an imino group of an imine compound, each being performed in the presence of the ruthenium complex represented by the general formula (1*), (1'), or (2*) and a hydrogen donor. The hydrogen donor is not particularly limited, as long as the hydrogen donor is one generally used for a hydrogen transfer reduction reaction, such as formic acid, a salt thereof, or isopropanol, which is an alcohol having a hydrogen atom at an α-position of a carbon atom substituted with a hydroxyl group. In addition, hydrogen gas can also be used as the hydrogen donor. In addition, the asymmetric reduction reaction is preferably performed in the presence of a base. The base is a tertiary organic amine such as trimethylamine, triethylamine, or triisopropylamine or an inorganic base such as LiOH, NaOH, KOH, or $K_2CO_3$. The base is preferably triethylamine. The base is used in an excessive amount relative to the ruthenium complex, and the amount is, for example, 1 to 100000 times of the amount of the ruthenium complex in terms of molar ratio. When triethylamine is used, triethylamine is preferably used in an amount 1 to 10000 times of the amount of the catalyst.

When formic acid is used as the hydrogen donor, an amine is preferably used as the base. In this case, formic acid and the amine may be added to the reaction system separately, or an azeotrope of formic acid and the amine prepared in advance may be used.

In general, in the reaction, the hydrogen donor can be used as the reaction solvent, when the hydrogen donor is liquid. It is also possible to use one of or a mixture of two or more of non-hydrogen-donating solvents such as toluene, tetrahydrofuran, acetonitrile, dimethylformamide, dimethyl sulfoxide, acetone, and methylene chloride as an auxiliary solvent for dissolving the raw material. In a case where a formate is used or the like, the reaction may also be performed in a two-layer system in which water is used as an auxiliary solvent for dissolving the formate in combination with an organic solvent. In this case, a phase transfer catalyst may be used in combination in order to accelerate the reaction. In addition, when hydrogen gas is used as the hydrogen donor, it is preferable to use an alcohol solvent such as methanol, ethanol, or isopropanol.

The amount of the ruthenium complex, which serves as a catalyst, used is selected such that the molar ratio (S/C) of a substrate (S) (a carbonyl compound or an imine) to the ruthenium metal atoms (C) can be in a range from 10 to 1000000, and preferably from 100 to 15000.

The amount of the hydrogen donor used is generally equimolar or more to the carbonyl compound or the imine. When formic acid or a salt thereof is used as the hydrogen donor, the amount is preferably 1.5 times by mole or more. In addition, the amount is preferably 20 times by mole or less, and more preferably 10 times by mole or less. On the other hand, when the hydrogen donor is isopropanol or the like, the hydrogen donor is used in large excess relative to the substrate from the viewpoint of the reaction equilibrium, and the amount used is generally in a range of 1000 times by mole or less.

The reaction temperature is not particularly limited, and is generally −20 to 100° C., and preferably 0 to 70° C. The reaction pressure is not particularly limited, and is generally 0.5 to 2 atm, and preferably normal pressure. In addition, when hydrogen gas is used, the reaction pressure is generally 5 MPa or less, and preferably 3 MPa or less. The reaction time is 1 to 100 hours, and generally 2 to 50 hours, although it varies depending on the molar ratio (S/C).

After the reaction, the formed optically active substance can be separated and purified by a common operation such as distillation, extraction, chromatography, or recrystallization.

EXAMPLES

Hereinafter, the present invention will be described in detail based on Examples. However, the present invention is not limited to these Examples.

Note that, in the following Examples and the like, NMR spectra used for identification of complexes and determination of purities thereof were measured with a Mercury Plus 300 4N model apparatus manufactured by Varian Technologies Japan Ltd., or Bruker BioSpin Avance III 500 System. For GC analysis, Chirasil-DEX CB (0.25 mm×25 m, 0.25 μm) (manufactured by Varian, Inc.) or HP-1 (0.32 mm×30 m, 0.25 μm) (manufactured by Agilent Technologies, Inc.) was used. For HPLC analysis, YMC-Pack Pro C18 (4.6×250 mm, 5 μm) (manufactured by YMC) or CHIRALPAK AS-H (4.6× 250 mm, 5 μm) was used. In addition, for MS measurement, JMS-T100 GCV manufactured by JEOL Ltd. or LCMS-IT-TOF manufactured by Shimadzu Corporation was used.

In addition, the meanings of abbreviations in Examples are as follows.

THF: tetrahydrofuran
Msdpen: N-methanesulfonyl-1,2-diphenylethylenediamine
Tsdpen: N-(p-toluenesulfonyl)-1,2-diphenylethylenediamine
DIPEA: diisopropylethylamine S/C represents a value represented by the number of moles of the ketone or imine substrate/the number of moles of the catalyst.

Example 1

Production of 4-(4-methylcyclohexa-1,4-dienyl)butan-1-ol and 4-(5-methylcyclohexa-1,4-dienyl)butan-1-ol

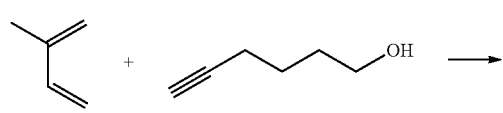

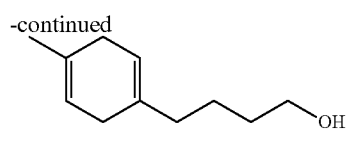

(1,4type)

+

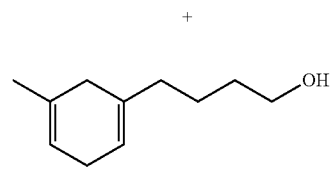

(1,5type)

In 45 mL of THF, 1,2-bis(diphenylphosphino)ethane (0.77 g, 1.93 mmol), cobalt bromide 0.41 (0.41 g, 1.87 mmol), zinc iodide (1.19 g, 3.73 mmol), and zinc (0.24 g, 3.67 mmol) were dissolved, followed by stirring at 70° C. for 15 minutes. After cooling to room temperature, isoprene (7.55 g, 110.83 mmol) was added. Then, 5-hexyn-1-ol (8.94 g, 91.09 mmol) was slowly added dropwise with cooling in a water bath. After stirring at 35° C. for 1 hour, the solvent was evaporated under reduced pressure, and the obtained residue was purified by silica gel column chromatography (hexane/ethyl acetate=3/1). Thus, 13.34 g of the title compounds, alcohols, were obtained as a colorless oily substance. Yield: 88.1% (isomer ratio: 1,4 type/1,5 type=77/23). Note that the following NMR spectrum data are those of the isomer mixture.

$^1$H-NMR (CDCl$_3$, 300 MHz): δ 5.61-5.57 (m, 2H'), 5.43-5.41 (m, 2H), 3.67-3.63 (m, 2H+2H'), 2.58 (brs, 4H), 2.10 (brs, 4H'), 2.08 (t, J=6.9 Hz, 2H'), 2.00 (t, J=7.2 Hz, 2H), 1.76 (s, 3H'), 1.67 (s, 3H), 1.61-1.43 (m, 5H+5H');

HRMS (ESI): calcd for C$_{11}$H$_{19}$O [M+H]$^+$ 167.1430, found 167.1432

Example 2

Production of 4-(4-methylcyclohexa-1,4-dienyl)butyl 4-methylbenzenesulfonate and 4-(5-methylcyclohexa-1,4-dienyl)butyl 4-methylbenzenesulfonate

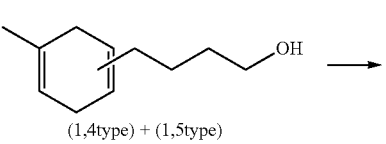

(1,4type) + (1,5type)

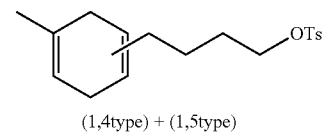

(1,4type) + (1,5type)

The alcohols (12.19 g, 73.32 mmol, isomer ratio: 1,4 type/1,5 type=77/23) obtained in Example 1, triethylamine (8.90 g, 87.98 mmol), and 1-methylimidazole (7.22 g, 87.98 mmol) were dissolved in 10 mL of toluene. With cooling in an ice-bath, a toluene solution (40 ml) of p-toluenesulfonyl chloride (15.94 g, 83.58 mmol) was slowly added dropwise, followed by stirring at room temperature for 1 hour. Tap water was added thereto, and the resultant layers were separated from each other. The obtained organic layer was washed with 2 M hydrochloric acid and tap water. The solvent was evaporated under reduced pressure, and the obtained residue was purified by silica gel column chromatography (hexane/ethyl acetate=20/1→4/1). Thus, 20.25 g of the title compounds, tosylates, were obtained as a colorless oily substance. Yield: 86.2% (isomer ratio: 1,4 type/1,5 type=77/23). Note that the following NMR spectrum data are those of the isomer mixture.

$^1$H-NMR (CDCl$_3$, 300 MHz): δ 7.80-7.77 (m, 2H+2H'), 7.36-7.33 (m, 2H+2H'), 5.58-5.56 (m, 1H'), 5.51-5.49 (m, 1H'), 5.39-5.38 (m, 1H), 5.35-5.34 (m, 1H), 4.05-4.01 (m, 2H+2H'), 2.53 (brs, 4H), 2.45 (s, 3H+3H'), 2.05 (brs, 4H'), 1.99 (t, J=7.4 Hz, 2H'), 1.91 (t, J=7.4 Hz, 2H), 1.76 (s, 3H'), 1.66 (s, 3H), 1.67-1.58 (m, 2H+2H'), 1.49-1.37 (m, 2H+2H');

HRMS (ESI): calcd for C$_{18}$H$_{24}$O$_3$SNa [M+Na]$^+$ 343.1338, found 343.1330

Example 3

Production of 4-methyl-N-((1S,2S)-2-(4-(4-methyl-cyclohexa-1,4-dienyl)butylamino)-1,2-diphenyl-ethyl)benzenesulfonamide and 4-methyl-N-((1S,2S)-2-(4-(5-methylcyclohexa-1,4-dienyl)butylamino)-1,2-diphenylethyl)benzenesulfonamide

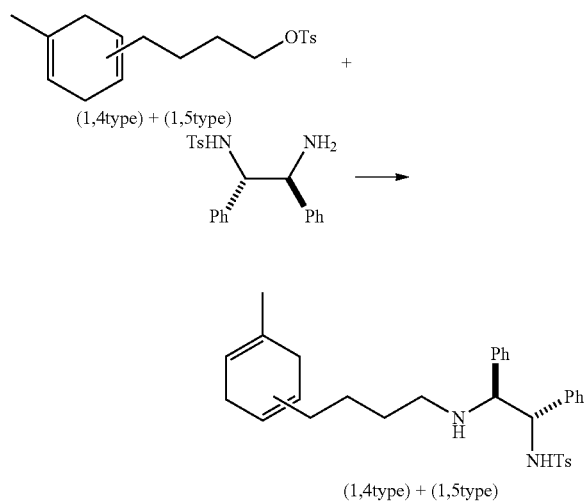

The tosylates (10.45 g, 32.61 mmol, isomer ratio: 1,4 type/1,5 type=77/23) obtained in Example 2 were dissolved in 40 ml of toluene, and DIPEA (4.79 g, 32.61 mmol) and (S,S)-TsDPEN (11.95 g, 32.61 mmol) were added thereto, followed by stirring at 135° C. for 14 hours. After that, the solvent was evaporated under reduced pressure, and the obtained residue was purified by silica gel column chromatography (hexane/ethyl acetate=2/1). Thus, 9.31 g of the title compounds were obtained as a yellow oily substance. Yield: 55.5% (isomer ratio: 1,4 type/1,5 type=77/23). Note that the following NMR spectrum data are those of the isomer mixture.

$^1$H NMR (CDCl$_3$, 300 MHz): δ 7.38-7.36 (m, 2H+2H'), 7.14-7.12 (m, 3H+3H'), 7.05-7.00 (m, 5H+5H'), 6.96-6.88 (m, 4H+4H'), 6.30 (brs, 1H+1H'), 5.60-5.58 (m, 1H'), 5.53-5.51 (m, 1H'), 5.41-5.40 (m, 1H), 5.37-5.36 (m, 1H), 4.24-4.22 (m, 1H+1H'), 3.60-3.58 (m, 1H+1H'), 2.55 (brs, 4H), 2.46-2.37 (m, 1H+1H'), 2.34 (s, 3H+3H'), 2.32-2.23 (m, 1H+1H'), 2.01 (brs, 4H), 2.01-1.88 (m, 2H+2H'), 1.77 (s, 3H'), 1.67 (s, 3H), 1.46-1.28 (m, 5H+5H');

HRMS (ESI): calcd for C$_{32}$H$_{39}$N$_2$O$_2$S [M+H]$^+$ 515.2727, found 515.2747

Example 4

Production of 4-methyl-N-((1S,2S)-2-(4-(4-methyl-cyclohexa-1,4-dienyl)butylamino)-1,2-diphenyl-ethyl)benzenesulfonamide hydrochloride and 4-methyl-N-((1S,2S)-2-(4-(5-methylcyclohexa-1,4-dienyl)butylamino)-1,2-diphenylethyl)benzenesulfonamide hydrochloride

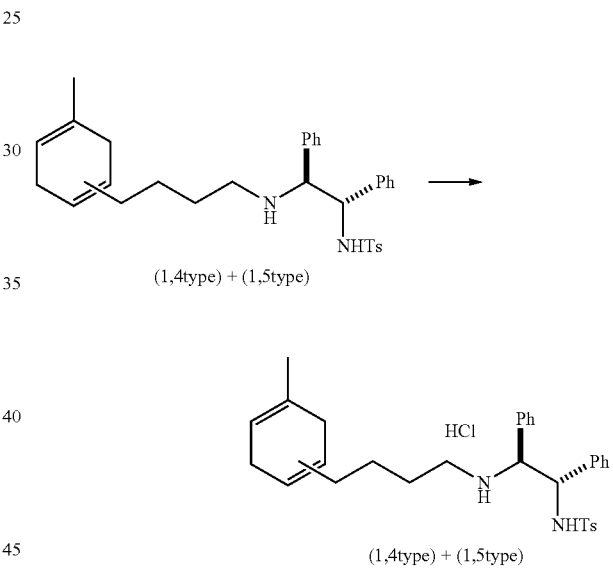

The amides (8.55 g, 16.61 mmol, isomer ratio: 1,4 type/1,5 type=77/23) obtained in Example 3 were dissolved in 33 ml of toluene. Under ice-cooling, a 1 M hydrochloric acid methanolic solution (3.46 g, 33.22 mmol) was added, followed by stirring at room temperature for 20 minutes. After that, the solvent was evaporated under reduced pressure. Thus, 8.85 g of the title compounds, diamine hydrochlorides, were obtained as a white solid. Yield: 96.7% (isomer ratio: 1,4 type/1,5 type=77/23). Note that the following NMR spectrum data are those of the isomer mixture.

$^1$H-NMR (d$_6$-DMSO, 300 MHz) δ: 9.61 (brs, 1H+1H'), 9.15 (brs, 1H+1H'), 8.85 (d, 1H+1H'), 7.29-6.79 (m, 14H+14H'), 5.55 (m, 1H'), 5.48 (m, 1H'), 5.36 (m, 1H), 5.31 (m, 1H), 4.82 (m, 1H+1H'), 4.54 (m, 1H+1H'), 2.66 (brs, 4H), 2.20 (s, 3H+3H'), 1.99 (brs, 4H'), 1.98-1.90 (m, 2H'), 1.90-1.82 (m, 2H), 1.71 (s, 3H'), 1.70-1.52 (m, 2H+2H'), 1.61 (s, 3H), 1.38-1.18 (m, 2H+2H');

HRMS (ESI): calcd for C$_{32}$H$_{39}$N$_2$O$_2$S [M−Cl]$^+$ 515.2727, found 515.2728

Example 5

Production of N-[(1S,2S)-1,2-diphenyl-2-(4-(4-methylphenyl)butylamino)-ethyl]-4-methylbenzenesulfonamide ammonium chloride ruthenium dimer and N-[(1S,2S)-1,2-diphenyl-2-(4-(3-methylphenyl)butylamino)-ethyl]-4-methylbenzenesulfonamide ammonium chloride ruthenium dimer

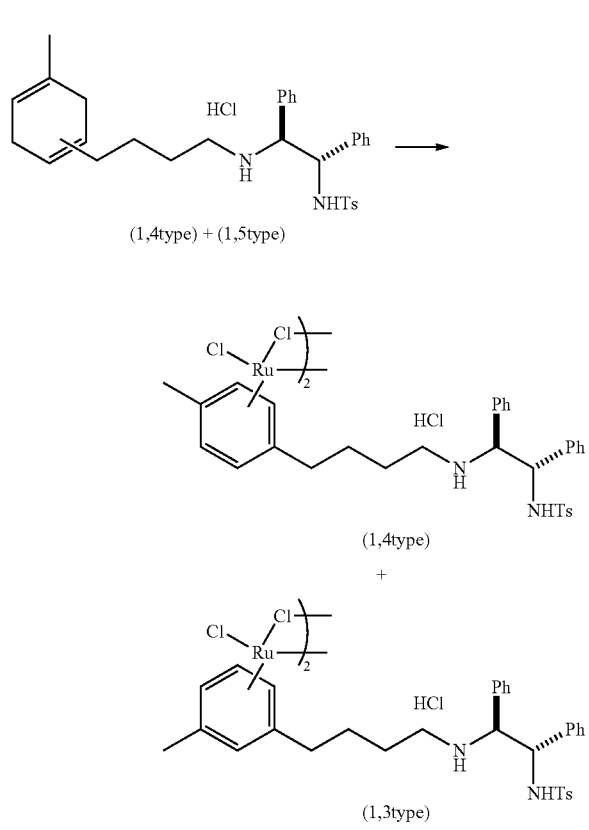

The hydrochlorides (7.42 g, 13.46 mmol, isomer ratio: 1,4 type/1,5 type=77/23) obtained in Example 4 and ruthenium trichloride.trihydrate (3.20 g, 12.25 mmol) were dissolved in a mixture solvent of 110 ml of 3-methoxypropanol and 37 ml of water, followed by stirring at 120° C. for 1 hour. The solvent was evaporated under reduced pressure, and diethyl ether was added to the obtained residue, followed by stirring at room temperature for 15 minutes. The precipitated crystals were filtered. Thus, 10.15 g of the title compounds, ruthenium dimers, were obtained. Yield: 52.3%. The following NMR spectrum data are those of the major product (1,4 type).

$^1$H NMR (d$_6$-DMSO, 500 MHz): δ 9.61 (brs, 2H), 9.11 (brs, 2H), 8.78 (d, J=9.1 Hz, 2H), 7.30-6.88 (m, 28H), 6.82-6.81 (m, 8H), 4.83 (m, 2H), 4.56 (m, 2H), 2.71 (brs, 4H), 2.35 (t, J=7.5 Hz, 4H), 2.22 (s, 6H), 2.10 (s, 6H), 1.80-1.60 (m, 4H), 1.60-1.42 (m, 4H);

HRMS (FD): calcd for C$_{32}$H$_{35}$ClN$_2$O$_2$RuS [M/2-2HCl]+ ·648.1156, found 648.1182

Example 6

Production of N-[(1S,2S)-1,2-diphenyl-2-(4-(4-methylphenyl)butylamino)-ethyl]-4-methylbenzenesulfonamide ammonium chloride ruthenium monomer and N-[(1S,2S)-1,2-diphenyl-2-(4-(3-methylphenyl)butylamino)-ethyl]-4-methylbenzenesulfonamide ammonium chloride ruthenium monomer

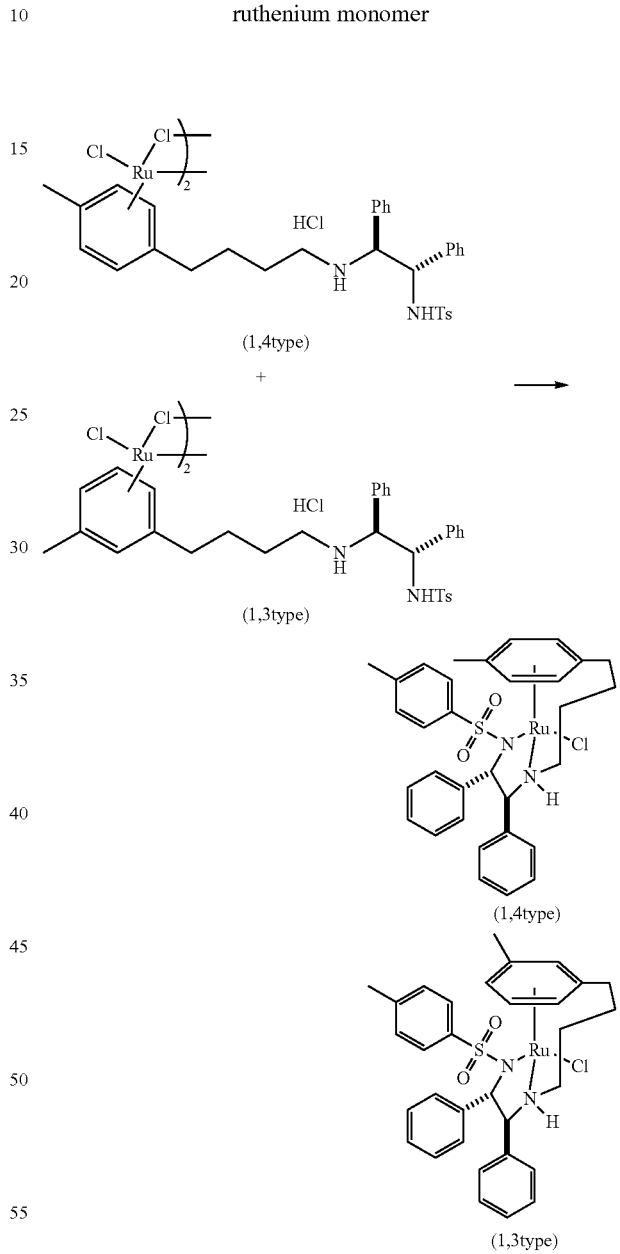

The ruthenium dimers (9.12 g, 6.32 mmol) obtained in Example 5 were dissolved in 155 ml of 2-propanol, and triethylamine (2.53 g, 25.29 mmol) was added thereto, followed by stirring at 60° C. for 1 hour. After that, the solvent was evaporated under reduced pressure, and the obtained residue was purified by silica gel chromatography (chloroform/methanol=20/1). Thus, 6.77 g of the title compounds, ruthenium monomers, were obtained. Yield: 82.6% (the chemical purity based on HPLC was 97.2%). The following NMR spectrum data are those of the major product (1,4 type).

¹H NMR (CD₂Cl₂, 500 MHz): δ 7.17 (d, J=7.9 Hz, 2H), 7.10-7.05 (m, 3H), 6.86 (d, J=7.9 Hz, 2H), 6.82-6.79 (m, 1H), 6.74 (d, J=6.4 Hz, 2H), 6.68 (dd, J=7.9 Hz, 2H), 6.56 (d, J=7.9 Hz, 2H), 6.18 (d, J=5.6 Hz, 1H), 5.55 (d, J=6.3 Hz, 1H), 5.35 (d, J=6.3 Hz, 1H), 5.29 (d, J=5.6 Hz, 1H), 4.73-4.70 (m, 1H), 3.97 (d, J=11.0 Hz, 1H), 3.81 (dd, J=11.0, 12.2 Hz, 1H), 3.52-3.47 (m, 1H), 3.13-3.07 (m, 1H), 2.85-2.81 (m, 1H), 2.75-2.69 (m, 1H), 2.44 (s, 3H), 2.26 (s, 3H), 2.28-2.17 (m, 1H), 2.15-2.04 (m, 1H), 1.96-1.88 (m, 1H), 1.67-1.60 (m, 1H);

HRMS (ESI): calcd for C₃₂H₃₆ClN₂O₂RuS [M+H]⁺ 649.1224, found 649.1224

Example 7

Production of N-((1S,2S)-2-(4-(4-methylcyclohexa-1,4-dienyl)butylamino)-1,2-diphenylethyl)methanesulfonamide and N-((1S,2S)-2-(4-(5-methylcyclohexa-1,4-dienyl)butylamino)-1,2-diphenylethyl)methanesulfonamide

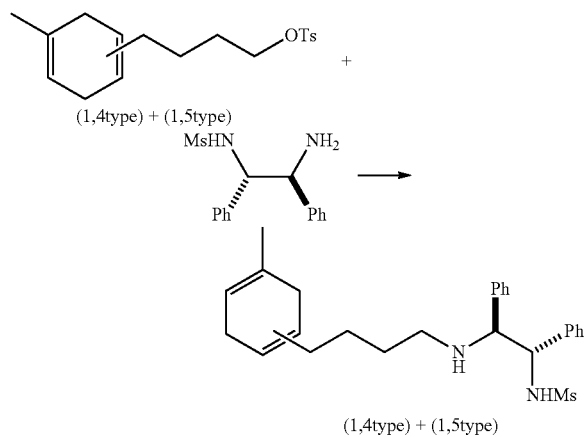

The tosylates (5.11 g, 15.95 mmol) obtained in Example 2 were dissolved in 20 ml of toluene, and DIPEA (2.05 g, 15.95 mmol) and (S,S)-MsDPEN (4.63 g, 15.95 mmol) were added thereto, followed by stirring at 135° C. for 16 hours. After that, the solvent was evaporated under reduced pressure, and the obtained residue was purified by silica gel column chromatography (hexane/ethyl acetate=2/1). Thus, 5.72 g of the title compounds, diamines, were obtained as a yellow oily substance. Yield: 81.8% (isomer ratio: 1,4 type/1,5 type=77/23). Note that the following NMR spectrum data are those of the mixture of the two isomers.

¹H NMR (CDCl₃, 300 MHz): δ 7.26-7.19 (m, 10H+10H'), 6.23 (brs, 1H+1H'), 5.59-5.58 (m, 1H'), 5.52-5.51 (m, 1H'), 5.40 (m, 1H), 5.36 (m, 1H), 4.47-4.44 (m, 1H+1H'), 3.75-3.72 (m, 1H+1H'), 2.55 (brs, 4H), 2.46-2.37 (m, 1H+1H'), 2.34 (s, 3H+3H'), 2.32-2.23 (m, 1H+1H'), 2.01 (brs, 4H'), 2.01-1.88 (m, 2H+2H'), 1.77 (s, 3H'), 1.67 (s, 3H), 1.46-1.28 (m, 5H+5H');

HRMS (ESI): calcd for C₂₆H₃₅N₂O₂S [M+H]⁺ 439.2414, found 439.2409

Example 8

Production of N-((1S,2S)-2-(4-(4-methylcyclohexa-1,4-dienyl)butylamino)-1,2-diphenylethyl)methanesulfonamide hydrochloride and N-((1S,2S)-2-(4-(5-methylcyclohexa-1,4-dienyl)butylamino)-1,2-diphenylethyl)methanesulfonamide hydrochloride

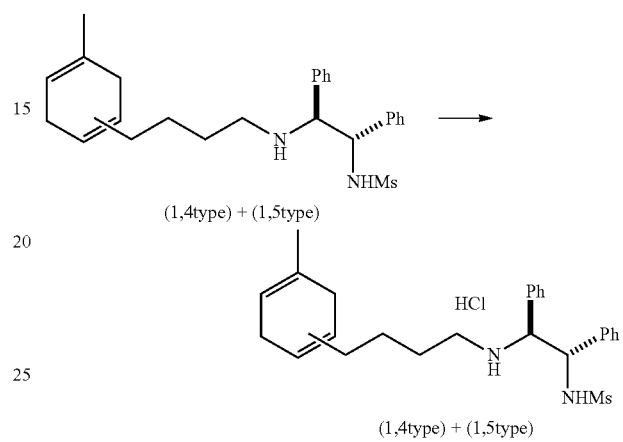

The diamines (5.11 g, 11.65 mmol) obtained in Example 7 were dissolved in 20 ml of toluene. Under ice-cooling, a 1 M hydrochloric acid methanolic solution (2.43 g, 23.30 mmol) was added thereto, followed by stirring at room temperature for 20 minutes. After that, the solvent was evaporated under reduced pressure. Thus, 5.14 g of the title compounds, diamine hydrochlorides, were obtained as a white solid. Yield: 92.9% (isomer ratio: 1,4 type/1,5 type=77/23). Note that the following NMR spectrum data are those of the mixture of the two isomers.

¹H-NMR (d₆-DMSO, 300 MHz) δ:9.94 (brs, 1H+1H'), 9.08 (brs, 1H+1H'), 8.34 (d, 1H+1H'), 7.39-7.00 (m, 10H+10H'), 5.54 (m, 1H'), 5.47 (m, 1H'), 5.35 (m, 1H), 5.30 (m, 1H), 4.90 (m, 1H+1H'), 4.56 (m, 1H+1H'), 2.72-2.56 (m, 6H+2H'), 2.47 (s, 3H+3H'), 1.98 (brs, 4H'), 1.93 (t, J=6.9 Hz, 2H'), 1.85 (t, J=7.2 Hz, 2H), 1.71 (s, 3H'), 1.70-1.52 (m, 2H+2H'), 1.61 (s, 3H), 1.38-1.18 (m, 2H+2H');

HRMS (ESI): calcd for C₂₆H₃₅N₂O₂S [M−Cl]⁺ 439.2414, found 439.2422

Example 9

Production of N-[(1S,2S)-1,2-diphenyl-2-(4-(4-methylphenyl)butylamino)-ethyl]-methanesulfonamide ammonium chloride ruthenium dimer and N-[(1S,2S)-1,2-diphenyl-2-(4-(3-methylphenyl)butylamino)-ethyl]-methanesulfonamide ammonium chloride ruthenium dimer

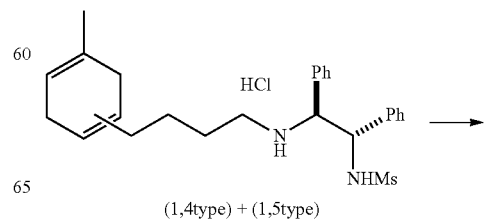

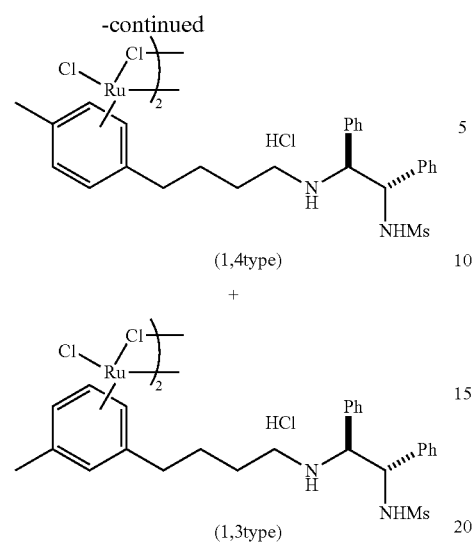

The diamine hydrochlorides (4.05 g, 8.52 mmol) obtained in Example 8 and ruthenium trichloride.trihydrate (2.03 g, 7.76 mmol) were dissolved in a mixture solvent of 60 ml of 3-methoxypropanol and 19 ml of water, followed by stirring at 120° C. for 1 hour. The solvent was evaporated under reduced pressure, and diethyl ether was added to the obtained residue, followed by stirring at room temperature for 15 minutes. The precipitated crystals were filtered. Thus, 5.49 g of the title compounds, ruthenium dimers, were obtained. Yield: 49.9%. The following NMR spectrum data are those of the major product (1,4 type).

$^1$H NMR ($d_6$-DMSO, 500 MHz): δ 9.87 (brs, 2H), 9.04 (brs, 2H), 8.27 (d, J=9.4 Hz, 2H), 7.39-7.01 (m, 20H), 5.76-5.73 (m, 8H), 4.91 (m, 2H), 4.59 (m, 2H), 2.70 (brs, 4H), 2.62 (s, 6H), 2.35 (t, J=7.7 Hz, 4H), 2.09 (s, 6H), 1.80-1.60 (m, 4H), 1.60-1.41 (m, 4H);

HRMS (FD): calcd for $C_{26}H_{31}ClN_2O_2RuS$ [M/2-2HCl]+ ·572.0841, found 572.0863

Example 10

Production of N-[(1S,2S)-1,2-diphenyl-2-(4-(4-methylphenyl)butylamino)-ethyl]-methanesulfonamide ammonium chloride ruthenium monomer and N-[(1S,2S)-1,2-diphenyl-2-(4-(3-methylphenyl)butylamino)-ethyl]-methanesulfonamide ammonium chloride ruthenium monomer

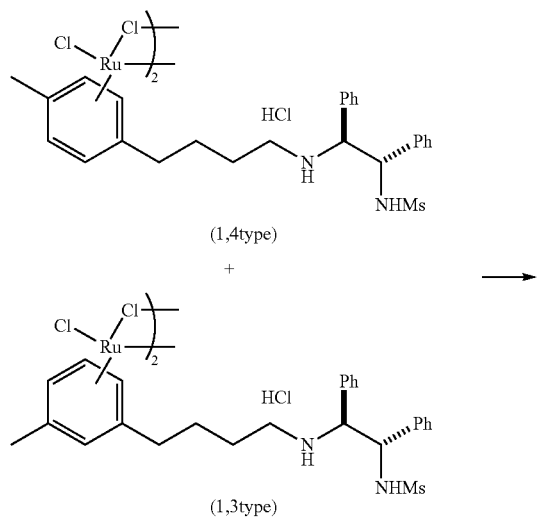

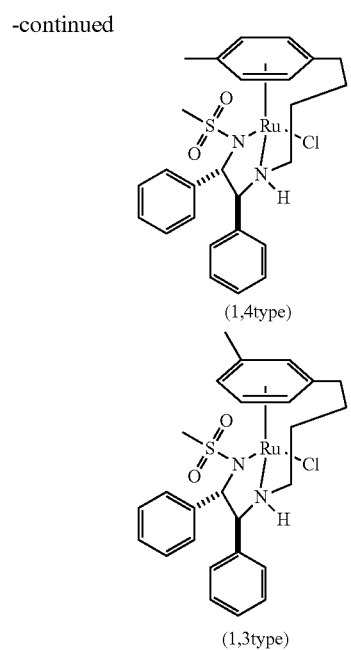

The ruthenium dimers (4.49 g, 3.48 mmol) of Example 9 were dissolved in 85 ml of 2-propanol, and triethylamine (1.45 g, 13.92 mmol) was added thereto, followed by stirring at 60° C. for 1 hour. After that, the solvent was evaporated under reduced pressure, and the obtained residue was purified by silica gel chromatography (chloroform/methanol=20/1). Thus, 3.38 g of the title compounds, ruthenium monomers, were obtained. Yield: 69.3% (the chemical purity based on HPLC was 98.2%). The following NMR spectrum data are those of the major product (1,4 type).

$^1$H NMR ($CD_2Cl_2$, 500 MHz): δ 7.17-7.13 (m, 3H), 7.10-7.07 (m, 3H), 6.97-6.95 (m, 2H), 6.85-6.83 (m, 2H), 5.84 (d, J=5.5 Hz, 1H), 5.51 (d, J=6.1 Hz, 1H), 5.46 (d, J=6.1 Hz, 1H), 5.38 (d, J=5.5 Hz, 1H), 4.41 (m, 1H), 4.01 (d, J=10.7 Hz, 1H), 3.86 (dd, J=10.7, 12.2 Hz, 1H), 3.43-3.38 (m, 1H), 3.12-3.07 (m, 1H), 2.80-2.71 (m, 2H), 2.47 (s, 3H), 2.37 (s, 3H), 2.25-2.17 (m, 1H), 2.11-2.02 (m, 1H), 1.98-1.90 (m, 1H), 1.77-1.68 (m, 1H);

HRMS (ESI): calcd for $C_{26}H_{32}ClN_2O_2RuS$ [M+H]+ 573.0911, found 573.0912

Example 11

Production of 4-(4,5-dimethylcyclohexa-1,4-dienyl)butan-1-ol

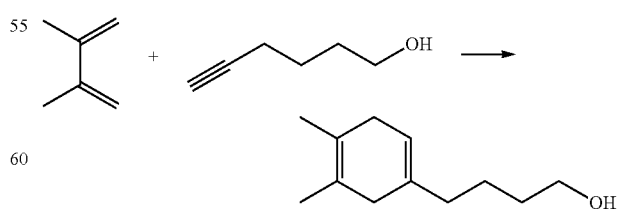

In 40 mL of THF, 1,2-bis(diphenylphosphino)ethane (800 mg, 2.00 mmol), cobalt bromide (437 mg, 2.00 mmol), zinc iodide (1.28 g, 4.00 mmol), and zinc (260 mg, 4.00 mmol) were dissolved, followed by stirring at 70° C. for 15 minutes.

After cooling to room temperature, 2,3-dimethyl-1,3-butadiene (9.86 g, 120 mmol) was added. Then, 5-hexyn-1-ol (9.8 g, 100 mmol) was slowly added dropwise with cooling in a water bath. After stirring at 35° C. for 1 hour, the solvent was evaporated under reduced pressure, and the obtained residue was purified by silica gel column chromatography (hexane/ethyl acetate=3/1). Thus, 11.5 g of the title compound, an alcohol, was obtained as a colorless oily substance. Yield: 63.4%.

$^1$H NMR (CDCl$_3$, 300 MHz): δ 5.56-5.41 (m, 1H), 3.67-3.63 (m, 2H), 2.61-2.48 (m, 2H), 2.11-1.98 (m, 3H), 1.63 (s, 6H), 1.79-1.46 (m, 4H), 1.28 (brs, 1H)

Example 12

Production of
4-(4,5-dimethylcyclohexa-1,4-dienyl)butyl
4-methylbenzenesulfonate

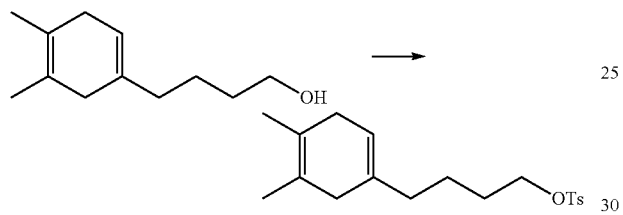

In 55 mL of toluene, 4-(4,5-dimethylcyclo-1,4-diene)butan-1-ol (11.0 g, 61.0 mmol), triethylamine (7.40 g, 73.08 mmol), and 1-methylimidazole (6.0 g, 73.0 mmol) were dissolved. With cooling in an ice-bath, a toluene solution (40 ml) of p-toluenesulfonyl chloride (13.9 g, 73.1 mmol) was slowly added dropwise, followed by stirring at room temperature for 1 hour. Tap water was added thereto, and the resultant layers were separated from each other. The obtained organic layer was washed with 2 M hydrochloric acid and tap water. The solvent was evaporated under reduced pressure, and the obtained residue was purified by silica gel column chromatography (hexane/ethyl acetate=20/1→4/1). Thus, 16.3 g of the title compound, a tosylate, was obtained. Yield: 80%.

$^1$H NMR (CDCl$_3$, 300 MHz): δ 7.80-7.77 (d, 2H), 7.36-7.33 (d, 2H), 5.40-5.28 (m, 1H), 4.05-4.00 (m, 2H), 2.53 (brs, 2H), 2.45 (s, 3H), 2.05-1.89 (m, 3H), 1.79-1.74 (m, 3H), 1.67 (s, 6H), 1.60-1.41 (m, 2H)

Example 13

Production of 4-methyl-N-((1S,2S)-2-(4-(4,5-dimethylcyclohexa-1,4-dienyl)butylamino)-1,2-diphenylethyl)benzenesulfonamide hydrochloride

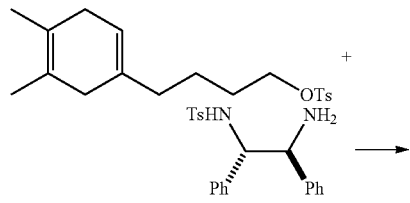

In 30 ml of toluene, 4-(4,5-dimethylcyclo-1,4-diene)butyl-p-toluenesulfonate (3.3 g, 9.87 mmol) was dissolved, and DIPEA (1.40 g, 10.79 mmol) and (S,S)-TsDPEN (3.3 g, 90.0 mmol) were added thereto, followed by stirring at 130° C. for 14 hours. After that, the solvent was evaporated under reduced pressure, and the obtained residue was purified by silica gel column chromatography (hexane/ethyl acetate=2/1). Then, a 1 M hydrochloric acid methanolic solution was added under ice-cooling, followed by stirring at room temperature for 20 minutes. After that, the solvent was evaporated under reduced pressure. Thus, 2.47 g of the title compound, a diamine hydrochloride, was obtained as a white solid. Yield: 44.3%.

$^1$H NMR (DMSO-d$_6$, 300 MHz): δ 9.80 (brs, 1H), 9.22 (brs, 1H), 9.01 (brs, 1H), 7.29-7.21 (m, 7H), 6.99-6.82 (m, 7H), 5.40-5.28 (m, 1H), 4.90-4.84 (m, 1H), 2.63 (brs, 2H), 2.40 (brs, 2H), 2.21 (s, 3H), 1.99-1.89 (m, 2H), 1.75-1.62 (m, 2H), 1.58 (s, 6H), 1.60-1.41 (m, 2H)

HRMS (ESI): calcd for C$_{33}$H$_{41}$N$_2$O$_2$S [M−Cl]$^+$ 529.2892, found 529.2892

Example 14

Production of N-[(1S,2S)-1,2-diphenyl-2-(4-(3,4-dimethylphenyl)butylamino)-ethyl]-4-methylbenzenesulfonamide ammonium chloride ruthenium dimer

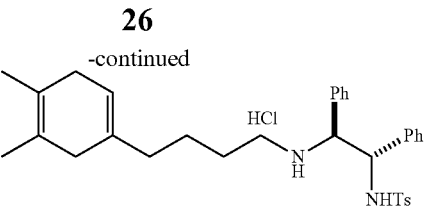

In a mixture solvent of 35 ml of 2-methoxyethanol and 3.7 ml of water, 4-methyl-N-((1S,2S)-2-(4-(4,5-dimethylcyclohexa-1,4-dienyl)butylamino)-1,2-diphenylethyl)benzenesulfonic acid hydrochloride (1.0 g, 1.77 mmol) and ruthenium trichloride.trihydrate (3.86 mg, 1.45 mmol) were dissolved, followed by stirring at 120° C. for 1 hour. The solvent was evaporated under reduced pressure, and diethyl ether was added to the obtained residue, followed by stirring at room temperature for 15 minutes. The precipitated crystals were filtered. Thus, 1.39 g of a ruthenium dimer was obtained. Yield: 82.5%.

$^1$H NMR (DMSO-d$_6$, 300 MHz): δ 9.80 (brs, 1H), 9.22 (brs, 1H), 8.91 (brs, 1H), 7.28-7.19 (m, 7H), 6.98 (d (J=8 Hz), 2H), 6.99-6.82 (m, 7H), 5.40-5.28 (m, 1H), 4.90-4.84 (m, 1H), 2.63 (brs, 2H), 2.40 (brs, 2H), 2.21 (s, 3H), 1.99-1.89 (m, 2H), 1.75-1.62 (m, 2H), 1.58 (s, 6H), 1.60-1.41 (m, 2H)

Example 15

Production of N-[(1S,2S)-1,2-diphenyl-2-(4-(3,4-dimethylphenyl)butylamino)-ethyl]-4-methylbenzenesulfonamide ammonium chloride ruthenium monomer

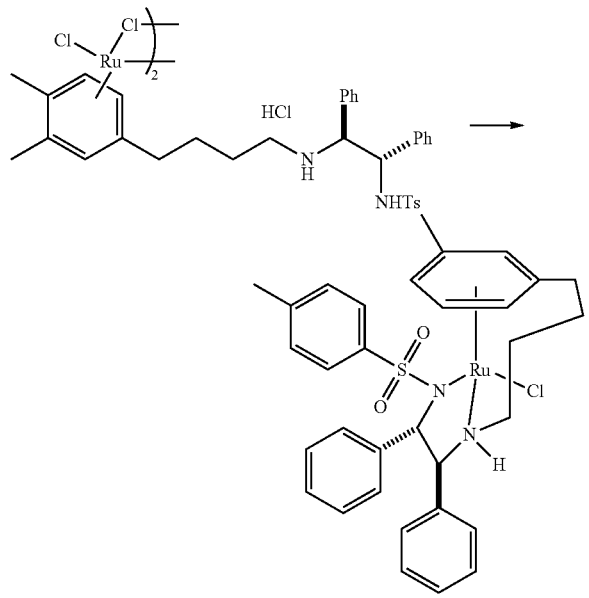

The ruthenium dimer (870 mg, 1.27 mmol) obtained in Example 14 was dissolved in 60 ml of 2-propanol, and triethylamine (514 mg, 5.07 mmol) was added thereto, followed by stirring at 60° C. for 1 hour. After that, the solvent was evaporated under reduced pressure, and the obtained residue was purified by silica gel chromatography (chloroform/methanol=20/1). Thus, 500 mg of the title compound, a ruthenium monomer, was obtained. Yield: 42.7%.

HRMS (ESI): calcd for $C_{33}H_{38}ClN_2O_2RuS$ $[M+H]^+$ 663.1381, found 663.1371

Example 16

Hydrogen Transfer Reaction to Acetophenone as Substrate Using N-[(1S,2S)-1,2-diphenyl-2-(4-(4-methylphenyl)butylamino)-ethyl]-4-methylbenzenesulfonamide ammonium chloride ruthenium monomer (hereinafter, RuCl(Tol-C4-teth-(S,S)-Tsdpen))

In a 25-ml Schlenk tube, 4.5 mg (0.00694 mmol, S/C=1000) of the complex, RuCl(Tol-C4-teth-(S,S)-Tsdpen), produced in Example 6, acetophenone (0.82 g, 6.86 mmol), and 3.4 ml of a formic acid-triethylamine (5:2) azeotrope were mixed with each other, and the reaction was allowed to proceed at 60° C. for 7 hours. GC analysis of the reaction liquid showed that (S)-1-phenylethanol was formed with a conversion of 99.5% and 96.5% ee.

Example 17

Hydrogen Transfer Reaction to Acetophenone as Substrate Using N-[(1S,2S)-1,2-diphenyl-2-(4-(4-methylphenyl)butylamino)-ethyl]-4-methylbenzenesulfonamide ammonium chloride ruthenium dimer In a 25-ml Schlenk tube, 4.9 mg (0.00339 mmol, S/C=1000) of the ruthenium dimer complex produced in Example 5, acetophenone (0.82 g, 6.86 mmol), and 3.4 ml of a formic acid-triethylamine (5:2) azeotrope were mixed with each other, and the reaction was allowed to proceed at 60° C. for 5 hours. GC analysis of the reaction liquid showed that (S)-1-phenylethanol was formed with a conversion of 98.9% and 96.6% ee.

Example 18

Hydrogen Transfer Reaction to Acetophenone as Substrate Using N-[(1S,2S)-1,2-diphenyl-2-(4-(4-methylphenyl)butylamino)-ethyl]-methanesulfonamide ammonium chloride ruthenium monomer (hereinafter, RuCl(Tol-C4-teth-(S,S)-Msdpen))

In a 25-ml Schlenk tube, the complex, RuCl(p-Tol-C4-teth-(S,S)-Msdpen), produced in Example 10 (4.0 mg, 0.00694 mmol, S/C=1000), acetophenone (0.82 g, 6.86 mmol), and 3.4 ml of a formic acid-triethylamine (5:2) azeotrope were mixed with each other, and the reaction was allowed to proceed at 60° C. for 7 hours. GC analysis of the reaction liquid showed that (S)-1-phenylethanol was formed with a conversion of 99.3% and 94.8% ee.

Example 19

Hydrogen Transfer Reaction to Acetophenone as Substrate Using N-[(1S,2S)-1,2-diphenyl-2-(4-(4-methylphenyl)butylamino)-ethyl]-methanesulfonamide ammonium chloride ruthenium dimer In a 25-ml Schlenk tube, 4.4 mg (0.00341 mmol, S/C=1000) of the ruthenium dimer complex produced in Example 9, acetophenone (0.82 g, 6.86 mmol), and 3.4 ml of a formic acid-triethylamine (5:2) azeotrope were mixed with each other, and the reaction was allowed to proceed at 60° C. for 5 hours. GC analysis of the reaction liquid showed that (S)-1-phenylethanol was formed with a conversion of 99.2% and 95.0% ee.

Comparative Example 1

Hydrogen Transfer Reaction to Acetophenone as Substrate Using RuCl((S,S)-Tsdpen)(mesitylene)

In a 15-ml Schlenk tube, 6.2 mg (0.01 mmol, S/C=500) of RuCl((S,S)-Tsdpen)(mesitylene), 0.67 ml (0.67 g, 5.0 mmol) of acetophenone, and 2.5 ml of a formic acid-triethylamine (5:2) azeotrope were mixed with each other. After purging with nitrogen, the reaction was allowed to proceed at 60° C. for 24 hours. GC analysis of the reaction liquid showed that (S)-1-phenylethanol was formed with a conversion of 52.3% and 93.0% ee.

Examples 20 to 35 and Comparative Examples 2 to 8

As Examples 20 to 35, hydrogen transfer reactions to ketones shown in Tables 1, 2, and 3 below were conducted by the same operation as in Examples 16 and 18. In these reactions, the catalyst ratios (S/C) were as shown in the tables, the reaction temperature was 60° C., and a formic acid-triethylamine (5:2) azeotrope was used as a hydrogen source in such an amount that the concentration of the substrate was 2 mol/L. The conversions and the optical purities were determined by analyzing the reaction liquids by GC after predetermined periods.

In addition, as Comparative Examples, results of reactions in which RuCl((S,S)-Tsdpen)(mesitylene) was used in the same manner are also shown in each table. Note that, in these tables, conv. represents the conversion of the ketone substrate, selec. represents the selectivity for the target product, % ee represents the optical purity, and S/C represents a value represented by the number of moles of the ketone substrate/the number of moles of the catalyst.

TABLE 1

| Ru complex/ketone substrate | F-phenyl methyl ketone (1) | Cl-phenyl methyl ketone (2) | MeO-phenyl methyl ketone (3) |
|---|---|---|---|
| Ex. 20 to 22 RuCl(Tol-C4-teth-(S,S)-Tsdpen | S/C = 1000, 5 h 98.7% conv. 89.8% ee | S/C = 1000, 8 h 99.1% conv. 83.6% ee | S/C = 1000, 24 h 99.8% conv. 92.4% ee |
| Ex. 23 to 25 RuCl(Tol-C4-teth-(S,S)-Msdpen | S/C = 1000, 5 h 99.2% conv. 89.3% ee | S/C = 1000, 8 h 99.5% conv. 88.9% ee | S/C = 1000, 24 h 96.8% conv. 89.0% ee |
| Comp. Ex. 2 to 4 RuCl((S,S)-Tsdpen) (mesitylene) | S/C = 500, 5 h 7.6% conv. 49.6% ee | S/C = 500, 8 h 3.4% conv. 14.8% ee | S/C = 500, 24 h 20.8% conv. 86.6% ee |

TABLE 2

| Ru complex/ketone substrate | 2'-MeO-2-hydroxyacetophenone (4) | α-chloroacetophenone (5) | propiophenone (6) |
|---|---|---|---|
| Ex. 26 to 28 RuCl(Tol-C4-teth-(S,S)-Tsdpen) | S/C = 1000, 2 h 100% conv. 81.4% ee | S/C = 1000, 1 h 100% conv. (81.6% selec.) 96.9% ee | S/C = 1000, 7 h 99.0% conv. 93.6% ee |
| Ex. 29 to 31 RuCl(Tol-C4-teth-(S,S)-Msdpen) | S/C = 1000, 2 h 100% conv. 80.5% ee | S/C = 1000, 1 h 98.7% conv. (72.5% selec.) 95.2% ee | S/C = 1000, 7 h 99.0% conv. 93.6% ee |
| Comp. Ex. 5 to 7 RuCl((S,S)-Tsdpen) (mesitylene) | S/C = 500, 2 h 0% conv. 0% ee | S/C = 500, 5 h 97.7% conv. (66.0% selec.) 90.9% ee | S/C = 500, 24 h 53.2% conv. 93.0% ee |

TABLE 3

| Ru complex/ketone substrate | 2-acetonaphthone (7) | 1-acetonaphthone (8) | benzosuberone (10) |
|---|---|---|---|
| Ex. 32 to 34 RuCl(Tol-C4-teth-(S,S)-Tsdpen | S/C = 1000 5 h 99.0% conv. 94.6% ee | S/C = 1000 24 h 88.6% conv. 81.1% ee | S/C = 1000 7 h 51.0% conv. 94.3% ee |
| Ex. 35 to 37 RuCl(Tol-C4-teth-(S,S)-Msdpen | S/C = 1000 5 h 98.8% conv. 92.9% ee | S/C = 1000 24 h 98.7% conv. 95.3% ee | S/C = 1000 7 h 57.3% conv. 96.1% ee |
| Comp. Ex. 8 to 10 RuCl((S,S)-Tsdpen) (mesitylene) | S/C = 500 24 h 28.1% conv. 90.6% ee | S/C = 500 24 h 15.0% conv. 65.8% ee | S/C = 500 24 h 1.9% conv. 51.5% ee |

Moreover, as Comparative Examples, results of hydrogen transfer reactions in which three known complexes shown below were used are also shown.

N-[(1S,2S)-1,2-diphenyl-2-(3-(4-methylphenyl)propylamino)-ethyl]-4-methylbenzenesulfonamide ammonium chloride ruthenium monomer and
N-[(1S,2S)-1,2-diphenyl-2-(3-(3-methylphenyl)propylamino)-ethyl]-4-methylbenzenesulfonamide ammonium chloride ruthenium monomer (hereinafter, referred to as RuCl(Tol-C3-teth-(S,S)-Tsdpen))

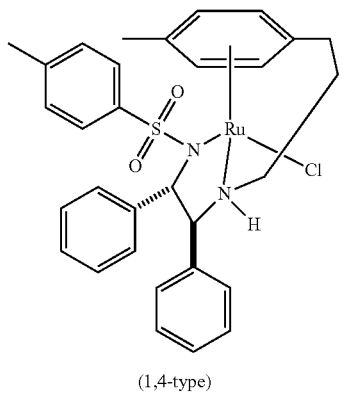

(1,4-type)

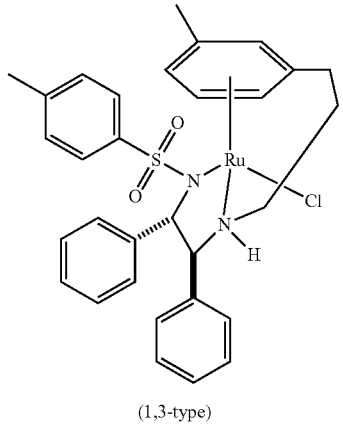

(1,3-type)

HRMS (ESI): calcd for $C_{31}H_{34}ClN_2O_2RuS$ [M+H]$^+$ 635.1072, found 635.1041

N-[(1S,2S)-1,2-diphenyl-2-(4-phenylbutylamino)-ethyl]-4-methylbenzenesulfonamide ammonium chloride ruthenium monomer (hereinafter, referred to as RuCl(benz-C4-teth-(S,S)-Tsdpen))

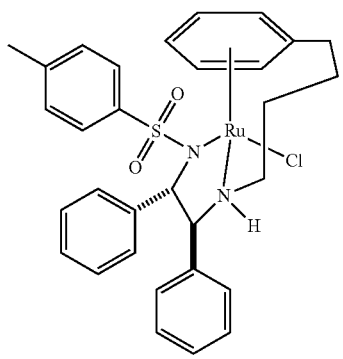

HRMS (ESI): calcd for $C_{31}H_{34}ClN_2O_2RuS$ [M+H]$^+$ 635.1072, found 635.1047

N-[(1S,2S)-1,2-diphenyl-2-(4-phenylpropylamino)-ethyl]-4-methylbenzenesulfonamide ammonium chloride ruthenium monomer (hereinafter, referred to as RuCl(benz-C3-teth-(S,S)-Tsdpen))

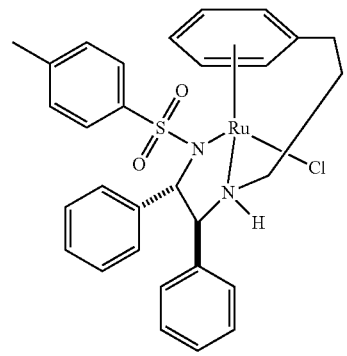

RuCl(Tol-C3-teth-(S,S)-Tsdpen) and RuCl(benz-C4-teth-(S,S)-Tsdpen) were produced by the method according to Scheme 1. Meanwhile, RuCl(benz-C3-teth-(S,S)-Tsdpen) was purchased from STREM CHEMICALS.

Comparative Example 11

Hydrogen transfer reaction to 2'-fluoroacetophenone as substrate using RuCl(Tol-C3-teth-(S,S)-Tsdpen)

In a 20-ml Schlenk tube, RuCl(Tol-C3-teth-(S,S)-Tsdpen) (4.20 mg, 0.00662 mmol, S/C=1000), 2'-fluoroacetophenone (0.91 g, 6.60 mmol), and 3.4 ml of a formic acid-triethylamine (5:2) azeotrope were mixed with each other, and the reaction was allowed to proceed at 60° C. for 5 hours. GC analysis of the reaction liquid showed that (S)-1-(2-fluorophenyl)ethanol was formed with a conversion of 99.2% and 82.0% ee.

Comparative Example 12

Hydrogen transfer reaction to 2'-fluoroacetophenone as substrate using RuCl(benz-C4-teth-(S,S)-Tsdpen)

In a 20-ml Schlenk tube, RuCl(benz-C3-teth-Tsdpen) (4.20 mg, 0.00662 mmol, S/C=1000), 2'-fluoroacetophenone (0.91 g, 6.60 mmol), and 3.4 ml of a formic acid-triethylamine (5:2) azeotrope were mixed with each other, and the reaction was allowed to proceed at 60° C. for 5 hours. GC analysis of the reaction liquid showed that (S)-1-(2-fluorophenyl)ethanol was formed with a conversion of 99.1% and 83.5% ee.

Comparative Example 13

Hydrogen transfer reaction to 2'-fluoroacetophenone as substrate using RuCl(benz-C3-teth-(S,S)-Tsdpen)

In a 20-ml Schlenk tube, RuCl(benz-C4-teth-Tsdpen) (4.10 mg, 0.00661 mmol, S/C=1000), 2'-fluoroacetophenone (0.91 g, 6.60 mmol), and 3.4 ml of a formic acid-triethylamine (5:2) azeotrope were mixed with each other, and the reaction was allowed to proceed at 60° C. for 5 hours. GC analysis of the reaction liquid showed that (S)-1-(2-fluorophenyl)ethanol was formed with a conversion of 99.2% and 83.6% ee.

Comparative Examples 14 to 22

Hydrogen transfer reactions to ketones shown in Table 4 below were conducted by the same operation as in Comparative Examples 11 to 13. Table 4 shows results thereof.

TABLE 4

| Ru complex/ketone substrate | (2) Cl-C6H4-C(O)CH3 | (3) MeO-C6H4-C(O)CH3 | (4) MeO-C6H4-C(O)CH2OH |
|---|---|---|---|
| Comp. Ex. 14 to 16 RuCl(Tol-C3-teth-(S,S)-Tsdpen) | S/C = 1000 8 h 99.5% conv. 73.8% ee | S/C = 1000 24 h 99.8% conv. 83.7% ee | S/C = 1000 2 h 100% conv. 70.7% ee |
| Comp. Ex. 17 to 19 RuCl(benz-C4-teth-(S,S)-Tsdpen | S/C = 1000 8 h 99.5% conv. 78.2% ee | S/C = 1000 24 h 99.1% conv. 78.9% ee | S/C = 1000 2 h 100% conv. 68.8% ee |
| Comp. Ex. 20 to 22 RuCl(benz-C3-teth-(S,S)-Tsdpen) | S/C = 1000 8 h 99.7% conv. 68.5% ee | S/C = 1000 24 h 99.6% conv. 69.8% ee | S/C = 1000 2 h 100% conv. 60.6% ee |

The results of Comparative Examples 11 to 22 showed that the complexes of the present invention were better in stereoselectivity and achieved higher enantiomeric excesses than the known complexes, RuCl(Tol-C3-teth-(S,S)-Tsdpen), RuCl(benz-C4-teth-(S,S)-Tsdpen), and RuCl(benz-C3-teth-(S,S)-Tsdpen). The ruthenium complexes of the present invention are extremely useful, because the ruthenium complexes make it possible to obtain target substances with high optical purities and high yields in hydrogen transfer reactions and hydrogenation reactions.

Example 38

Hydrogen Transfer Reaction to (E)-N-(3,4-dihydronaphthalene-1(2H)-ylidene)-1-phenylmethanamine using RuCl(Tol-C4-teth-(S,S)-Tsdpen)

In a 20-ml Schlenk tube, 3.7 mg (0.0057 mmol, S/C=300) of RuCl(Tol-C4-teth-(S,S)-Tsdpen), 0.40 g (1.70 mmol) of the imine in the title, 3.4 ml of dichloromethane, and 0.86 ml of a formic acid-triethylamine (5:2) azeotrope were mixed with each other, and the reaction was allowed to proceed at 30° C. for 20 hours. GC analysis of the reaction liquid showed that optically active N-benzyl-1,2,3,4-tetrahydronaphthalene-1-amine was formed with a conversion of 100% and 75.2% ee.

Example 39

Asymmetric hydrogenation of 4-chromanone using RuCl(Tol-C4-teth-(S,S)-Tsdpen)

In a 100-ml autoclave, 3.1 mg (0.00478 mmol, S/C=1000) of RuCl(Tol-C4-teth-(S,S)-Tsdpen) was placed, followed by purging with nitrogen. Subsequently, 0.72 g (5.0 mmol) of 4-chromanone and 4.4 ml of methanol were added thereto, and hydrogen was introduced to a pressure of 3.0 MPa, followed by stirring at 60° C. for 19 hours. The result of GC analysis of the reaction liquid showed that (S)-4-chromanol was obtained with a conversion of 100% and an optical purity of 97.9% ee.

Example 40

Asymmetric hydrogenation of 4-chromanone using RuCl(Tol-C4-teth-(S,S)-Msdpen)

In a 100-ml autoclave, 2.8 mg (0.00489 mmol, S/C=1000) of RuCl(Tol-C4-teth-(S,S)-Msdpen) was placed, followed by purging with nitrogen. Subsequently, 0.72 g (5.0 mmol) of 4-chromanone and 4.4 ml of methanol were added thereto, and hydrogen was introduced to a pressure of 3.0 MPa, followed by stirring at 60° C. for 19 hours. The result of GC analysis of the reaction liquid showed that (S)-4-chromanol was obtained with a conversion of 100% and an optical purity of 97.6% ee.

Example 41

Production of RuBF$_4$ (Tol-C4-teth-(S,S)-Tsdpen)

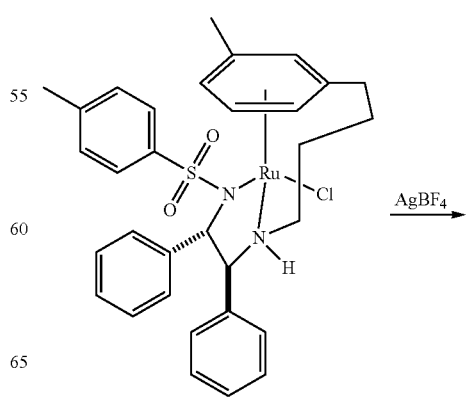

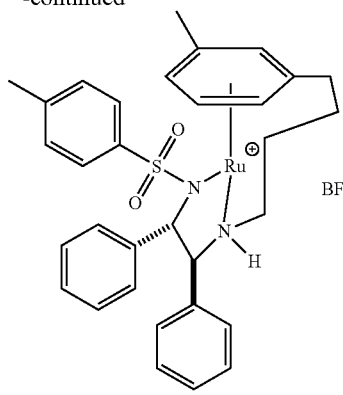

In a 50-ml Schlenk tube, 0.26 g (0.4 mmol, 1 eq) of RuCl (Tol-C4-teth-(S,S)-Tsdpen), 0.093 g (0.48 mmol, 1.2 eq) of AgBF$_4$, 8 ml of dichloromethane, and 8 ml of methanol were mixed with each other, followed by stirring at room temperature for 1 hour. The reaction solution was filtered through Celite, and the filtrate was evaporated to dryness. Thus, 0.28 g of the target complex, RuBF$_4$(Tol-C4-teth-(S,S)-Tsdpen), was obtained (yield: 98%).

HRMS (ESI): calcd for $C_{33}H_{39}ClN_2O_2RuS$ [M-BF$_4$]$^+$ 629.1770, found 629.1768

INDUSTRIAL APPLICABILITY

The present invention provides a novel ruthenium complex. The ruthenium complex of the present invention has an extremely high catalytic activity, and is hence useful as various hydrogenation catalysts. Furthermore, the ruthenium complex of the present invention is excellent in stereoselectivity, and hence useful as a catalyst for asymmetric reduction which achieves a high enantiomeric excess. Therefore, the present invention provides a ruthenium complex useful in the field of the industrial chemistry.

The invention claimed is:

1. A ruthenium complex represented by the following general formula (2*), or a salt thereof:

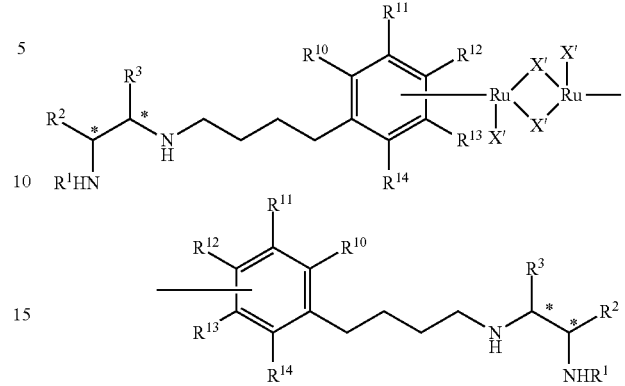

(2*)

wherein each * represents an asymmetric carbon atom, $R^1$ represents an alkyl group having 1 to 10 carbon atoms; an alkanesulfonyl group having 1 to 10 carbon atoms and optionally substituted with a halogen atom; an arenesulfonyl group optionally substituted with an alkyl group having 1 to 10 carbon atoms, a halogenated alkyl group having 1 to 10 carbon atoms, or a halogen atom; an alkoxycarbonyl group having 2 to 11 carbon atoms in total; or a benzoyl group optionally substituted with an alkyl group having 1 to 10 carbon atoms, $R^2$ and $R^{3'}$ each independently represent an alkyl group having 1 to 10 carbon atoms; a phenyl group optionally substituted with an alkyl group having 1 to 10 carbon atoms, an alkoxy group having 1 to 10 carbon atoms, or a halogen atom; or a cycloalkyl group having 3 to 8 carbon atoms, or $R^2$ and $R^3$ may together form a ring, $R^{10}$ to $R^{14}$ each independently represent a hydrogen atom, an alkyl group having 1 to 10 carbon atoms, an alkoxy group having 1 to 10 carbon atoms, or a trialkylsilyl group, provided that the case where all of $R^{10}$ to $R^{14}$ simultaneously represent hydrogen atoms is excluded, and X' represents a halogen atom.

2. A catalyst for asymmetric reduction, consisting of the ruthenium complex according to claim 1.

* * * * *